(12) United States Patent
Chapin et al.

(10) Patent No.: US 9,101,724 B2
(45) Date of Patent: Aug. 11, 2015

(54) PEN INJECTION DEVICE NEEDLE DISPENSING AND STORING APPARATUS

(75) Inventors: David S. Chapin, Raleigh, NC (US); Daniel M. Stipe, Raleigh, NC (US); Ryan Schoonmaker, San Marcos, CA (US); Cole Constantineau, Cambridge, MA (US); Michel Bruehwiler, Newton, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1038 days.

(21) Appl. No.: 13/205,561

(22) Filed: Aug. 8, 2011

(65) Prior Publication Data

US 2012/0041382 A1    Feb. 16, 2012

Related U.S. Application Data

(60) Provisional application No. 61/344,538, filed on Aug. 16, 2010, provisional application No. 61/344,540, filed on Aug. 16, 2010.

(51) Int. Cl.
*A61M 5/32* (2006.01)
*A61M 5/00* (2006.01)

(52) U.S. Cl.
CPC ............. *A61M 5/3205* (2013.01); *A61M 5/002* (2013.01); *A61M 5/003* (2013.01); *A61M 5/321* (2013.01); *A61M 5/3202* (2013.01)

(58) Field of Classification Search
CPC ... A61M 5/002; A61M 5/003; A61M 5/3202; A61M 5/3205; A61M 5/321
USPC ........................... 604/192–197; 206/363–370
See application file for complete search history.

(56) References Cited

U.S. PATENT DOCUMENTS

| | | | |
|---|---|---|---|
| 5,545,145 A * | 8/1996 | Clinton et al. | 604/192 |
| D386,526 S * | 11/1997 | Ito | D19/53 |
| 5,829,589 A | 11/1998 | Nguyen et al. | |
| 5,873,462 A | 2/1999 | Nguyen et al. | |
| 6,880,701 B2 | 4/2005 | Bergeron et al. | |
| 6,889,830 B2 | 5/2005 | Bergeron et al. | |
| 6,923,319 B1 | 8/2005 | Erickson et al. | |
| 7,134,550 B2 | 11/2006 | Groth | |
| 7,780,637 B2 | 8/2010 | Jerde et al. | |

(Continued)

FOREIGN PATENT DOCUMENTS

| | | |
|---|---|---|
| EP | 0697222 B1 | 2/1999 |
| FR | 2671730 B1 | 4/1993 |

(Continued)

*Primary Examiner* — Rebecca E Eisenberg
(74) *Attorney, Agent, or Firm* — Roylance, Abrams, Berdo & Goodman, L.L.P.

(57) ABSTRACT

An apparatus is disclosed for storing and dispensing pen needles for an injection device, including a case having dispensing and storage ends for dispensing and storing a plurality of pen needles and a plurality of needle cover units, each pen needle having a patient end and a hub for connection to the injection device, and each needle cover unit having a needle-covering portion for covering a patient end and a hub-covering portion for covering a hub. A needle-covering portion covering the needle of one pen needle is coupled with a hub-covering portion covering a hub of another pen needle. Prior to use, a hub-covering portion covering the hub of a pen needle is exposed to an outside at the dispensing end of the case, and subsequent to use, the pen needle is stored in the storage end of the case.

26 Claims, 28 Drawing Sheets

(56) References Cited

U.S. PATENT DOCUMENTS

| | | |
|---|---|---|
| 7,871,397 B2 | 1/2011 | Schraga |
| 8,181,779 B2 * | 5/2012 | Iio et al. .................. 206/366 |
| 2003/0015444 A1 | 1/2003 | Molin et al. |
| 2008/0154192 A1 | 6/2008 | Schraga |
| 2010/0063457 A1 | 3/2010 | Crossman |
| 2011/0060292 A1 | 3/2011 | Schraga |
| 2011/0077615 A1 | 3/2011 | Schraga |

FOREIGN PATENT DOCUMENTS

| | | |
|---|---|---|
| GB | 2437923 A | 11/2007 |
| WO | WO0187387 A1 | 11/2001 |
| WO | WO03063936 A1 | 8/2003 |

* cited by examiner

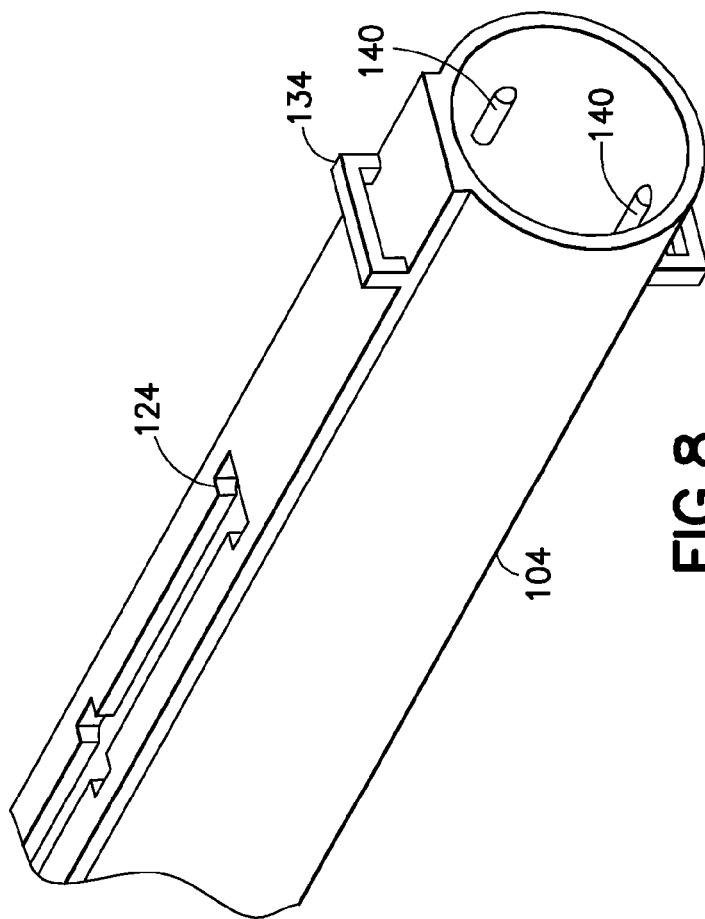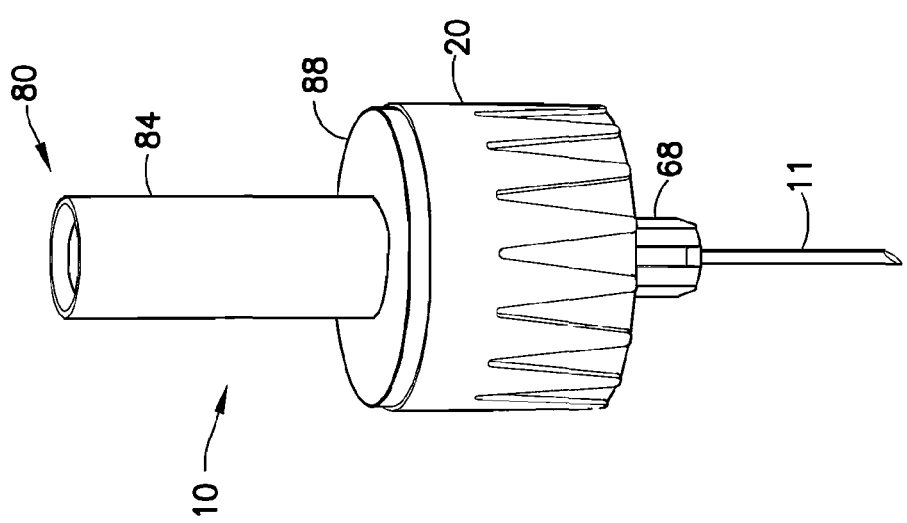

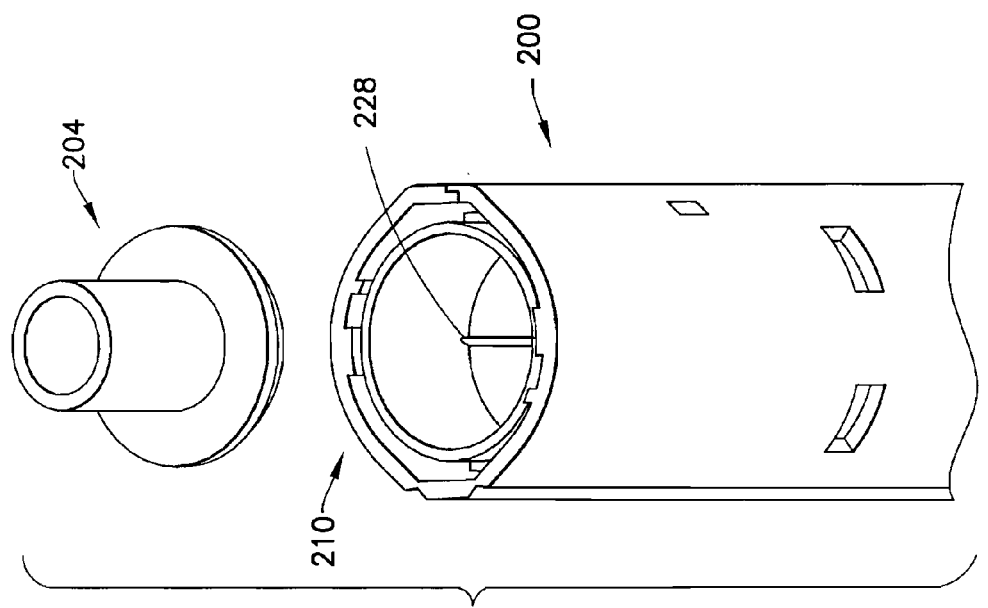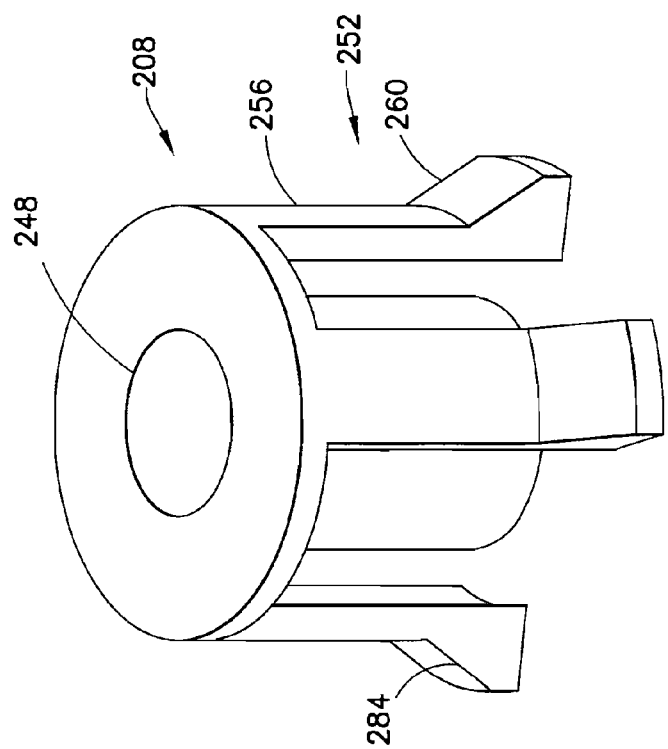

PEN INJECTION DEVICE NEEDLE DISPENSING AND STORING APPARATUS

CROSS-REFERENCE TO RELATED APPLICATIONS

This application claims priority under 35 USC §119(e) from U.S. Provisional Patent Application Ser. No. 61/344,538, filed on Aug. 16, 2010, and from U.S. Provisional Patent Application Ser. No. 61/344,540, filed on Aug. 16, 2010, the disclosures of both applications being incorporated herein by reference in their entirety.

BACKGROUND OF THE INVENTION

1. Field of the Invention

The present invention relates to needles for a pen injection device, and more particularly, to an apparatus for dispensing and storing needles for a pen injection device.

2. Description of the Related Art

Medication delivery pens are used for self-injection of precisely measured doses of medication. Pens are widely used, for example, by diabetics to self-inject insulin. A typical medication delivery pen includes a cartridge that contains a volume of liquid medication sufficient for several doses. Using a pen needle attached to the pen device, the dose is injected into a tissue area, such as the intramuscular tissue layer, the subcutaneous tissue layer, or the intradermal tissue layer.

The assembly and operation of a typical pen injection device is described in commonly-assigned U.S. Pat. No. 7,645,264, which is hereby incorporated by reference in its entirety.

Pen injection devices, such as an exemplary pen injector 50, as shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is employed by the user to securely hold the pen injector 50 in a shirt pocket, purse, or other suitable location.

FIG. 2 is an exploded view of the exemplary drug delivery pen 50 shown in FIG. 1. The dose knob/button 24 has a dual purpose and is used to both set the dosage of the medication to be injected and to inject the dosed medicament via a lead screw 7 and stopper 15 from a medicament cartridge 12, which is attached to the drug delivery pen through a lower housing 17. The medicament cartridge 12 is typically a glass tube sealed at one end with a septum 16 and at the other end with the stopper 15. In standard drug delivery pens, the dosing and delivery mechanisms are all found within the outer sleeve 13. Those mechanisms are not described in greater detail herein as they are understood by those knowledgeable of the art.

A pen needle 10 includes a hub 20, a patient needle 11 extending from a patient end of the pen needle, and a septum-penetrating needle cannula 18 disposed within the hub 20 on a non-patient side thereof. The septum-penetrating needle cannula 18 is in fluid communication with the patient needle 11. The hub 20 is preferably screwed onto the lower housing 17, although other attachment means can be used such as attaching directly to the medicament cartridge 12. In attaching the hub 20 to the lower housing 17 or medicament cartridge 12, the septum-penetrating cannula 18 pierces the septum 16, but the septum 16 does not move relative to the medicament cartridge 12. The stopper 15, however, is axially displaceable within the medicament cartridge 12 while maintaining a fluid-tight seal. The distal movement of the plunger or stopper 15 within the medicament cartridge 12 (due to advancement of the lead screw 7) causes medication to be forced into the patient needle 11 of the hub 20. The illustrated pen needle 10 is one example of a pen needle.

To protect a user, or anyone who handles the pen injector 50, an outer shield 29, which attaches to the hub 20, covers the hub 20. The outer shield 29 can also be used as a handle or grip to screw hub 20 onto or off of pen injector 50. An inner shield 28 covers the patient needle 11 within the outer shield 29. The inner shield 28 can be secured to the hub 20 to cover the patient needle 11 by any suitable means, such as an interference fit or a snap fit. The outer shield 29 and inner shield 28 are removed prior to use. The cap 21 fits snugly against outer sleeve 13 to allow a user to securely carry the pen injection device 50.

Pen needles are usually sold individually packaged inside a plastic cover (such as outer shield 29) with a label covering the opening in the cover to provide a sterility barrier. Recent market research indicates that consumers would prefer a multiple-needle package configuration that includes some provision for containing used pen needles after use. Accordingly, a need exists for a needle dispensing and storing apparatus that stores a plurality of pen needles before and after their use.

SUMMARY OF EMBODIMENTS OF THE INVENTION

It is an aspect of the present invention to provide an apparatus for storing pen needles. More specifically, it is an aspect of the present invention to provide an apparatus for storing pen needles prior to their use as well as subsequent to their use. Additionally, it is an aspect of the present invention to provide an apparatus for dispensing pen needles for use with a pen injection device.

The foregoing and/or other aspects of the present invention are achieved by providing an apparatus for storing and dispensing pen needles for an injection device, including a case having dispensing and storage ends for dispensing and storing a plurality of pen needles and a plurality of needle cover units, each pen needle having a patient end and a hub for connection to the injection device, and each needle cover unit having a needle-covering portion for covering a patient end and a hub-covering portion for covering a hub. A needle-covering portion covering the needle of one pen needle is coupled with a hub-covering portion covering a hub of another pen needle. Prior to use, at least a hub-covering portion covering the hub of a pen needle is exposed to an outside at the dispensing end of the case, and subsequent to use, at least the pen needle is stored in the storage end of the case.

The foregoing and/or other aspects of the present invention are also achieved by providing a method for dispensing and storing needle cover units and pen needles for an injection device, each pen needle having a patient end and a hub for connection to the injection device, and each needle cover unit having a needle-covering portion for covering a patient end and a hub-covering portion for covering a hub, the pen needles and needle covering units having a first orientation relative to the case at a dispensing end of the case. The method includes the operations of, at the dispensing end of a case, removing a needle cover unit from a pen needle in a dispensing position; connecting the injection device to the hub of the pen needle; at a storage end of the case, inserting a needle cover unit in a second orientation opposite to the first orientation; and inserting the pen needle into the storage end of the case in the second orientation, to cover the patient end of the pen needle with the needle covering portion of the needle cover unit.

The foregoing and/or other aspects of the present invention are also achieved by providing a method for dispensing and storing needle cover units and pen needles for an injection device, each pen needle having a patient end and a hub for connection to the injection device, and each needle cover unit having a needle-covering portion for covering a patient end and a hub-covering portion for covering a hub. The method includes the operations of, at the dispensing end of a case, removing a hub-covering portion of a needle cover unit from a pen needle in a dispensing position; connecting the injection device to the hub of the pen needle; and removing the pen needle, wherein removing the pen needle in the dispensing position automatically advances an unused pen needle and a needle cover unit toward the dispensing end of the case.

The foregoing and/or other aspects of the present invention are also achieved by providing an apparatus for storing and dispensing pen needles for an injection device, the apparatus including a case having dispensing and storage ends for dispensing and storing a plurality of pen needles and a plurality of needle cover units, each pen needle having a patient end and a hub for connection to the injection device, and each needle cover unit having a needle-covering end for covering a patient end and a hub-covering end for covering a hub. A needle cover unit covers a hub of a pen needle prior to connection of the pen needle to the injection device, and the needle cover unit covers the patient end of the pen needle during storage in the storage end of the case.

The foregoing and/or other aspects of the present invention are also achieved by providing an apparatus for storing and dispensing pen needles for a pen injection device, the apparatus including a plurality of pen needles, each having a patient end and a hub for connection to the pen injection device; a plurality of needle covers for covering the patient end of the pen needle; a plurality of hub covers, each having a first end for receiving a needle cover and a second end for covering a hub; and a case for storing and dispensing the pluralities of pen needles and needle covers, the case having dispensing and storage ends. Prior to use, a hub cover is exposed to an outside of the case at the dispensing end of the case, with the hub cover covering the hub of one of the plurality of pen needles in a dispensing position. Subsequent to the removal of the exposed hub cover, removal of the pen needle in the dispensing position from the case automatically moves the remaining hub covers, pen needles, and needle covers toward the dispensing end of the case and creates a space in the case at the storage end of the case for insertion of the removed pen needle.

Additional and/or other aspects and advantages of the present invention will be set forth in part in the description that follows and, in part, will be apparent from the description, or may be learned by practice of the invention.

BRIEF DESCRIPTION OF THE DRAWINGS

The above and/or other aspects and advantages of embodiments of the invention will become apparent and more readily appreciated from the following detailed description, taken in conjunction with the accompanying drawings, in which:

FIG. 6 is a perspective view of the pen needle and needle cover of FIG. 3 engaged to cover a non-patient end of the pen needle;

FIG. 8 is a perspective view of a dispensing end of the case of FIG. 7;

FIG. 25 is a perspective view of a separator in accordance with an embodiment of the present invention;

FIG. 26 is a partial perspective view of the hub cover of FIG. 22 removed from the case of FIG. 18;

DETAILED DESCRIPTION OF EMBODIMENTS OF THE PRESENT INVENTION

Figure 1:
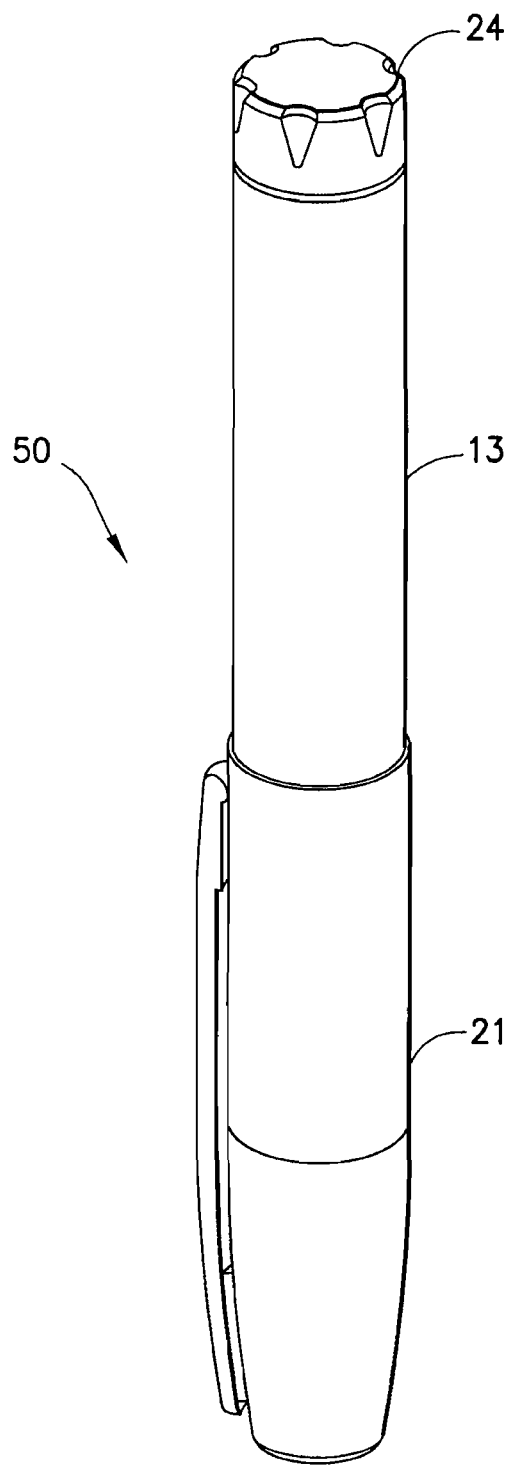
FIG. 1 is a perspective view of an exemplary drug delivery pen.

Reference will now be made in detail to embodiments of the present invention, examples of which are illustrated in the accompanying drawings, wherein like reference numerals refer to the like elements throughout. The embodiments described exemplify, but do not limit the present invention by referring to the drawings. As will be understood by one skilled in the art, terms such as up, down, bottom, and top are relative, and are employed to aid illustration, but are not limiting.

As noted above, the pen needle 10 includes the hub 20, and a patient needle 11. The septum-penetrating needle cannula 18 disposed within the non-patient end of the hub 20 fluidly communicates with the patient needle 11, and the interior of the non-patient end of the hub 20 includes threads or other features for connection with the pen injector (for example, pen injector 50). In these or other exemplary embodiments of the present invention the pen needle can omit one or more of the above features as long as sterility of both the patient and non-patient ends of the cannula is maintained. For example, an exemplary pen needle can also be provided having a hub and cannula assembly only.

Figure 2:
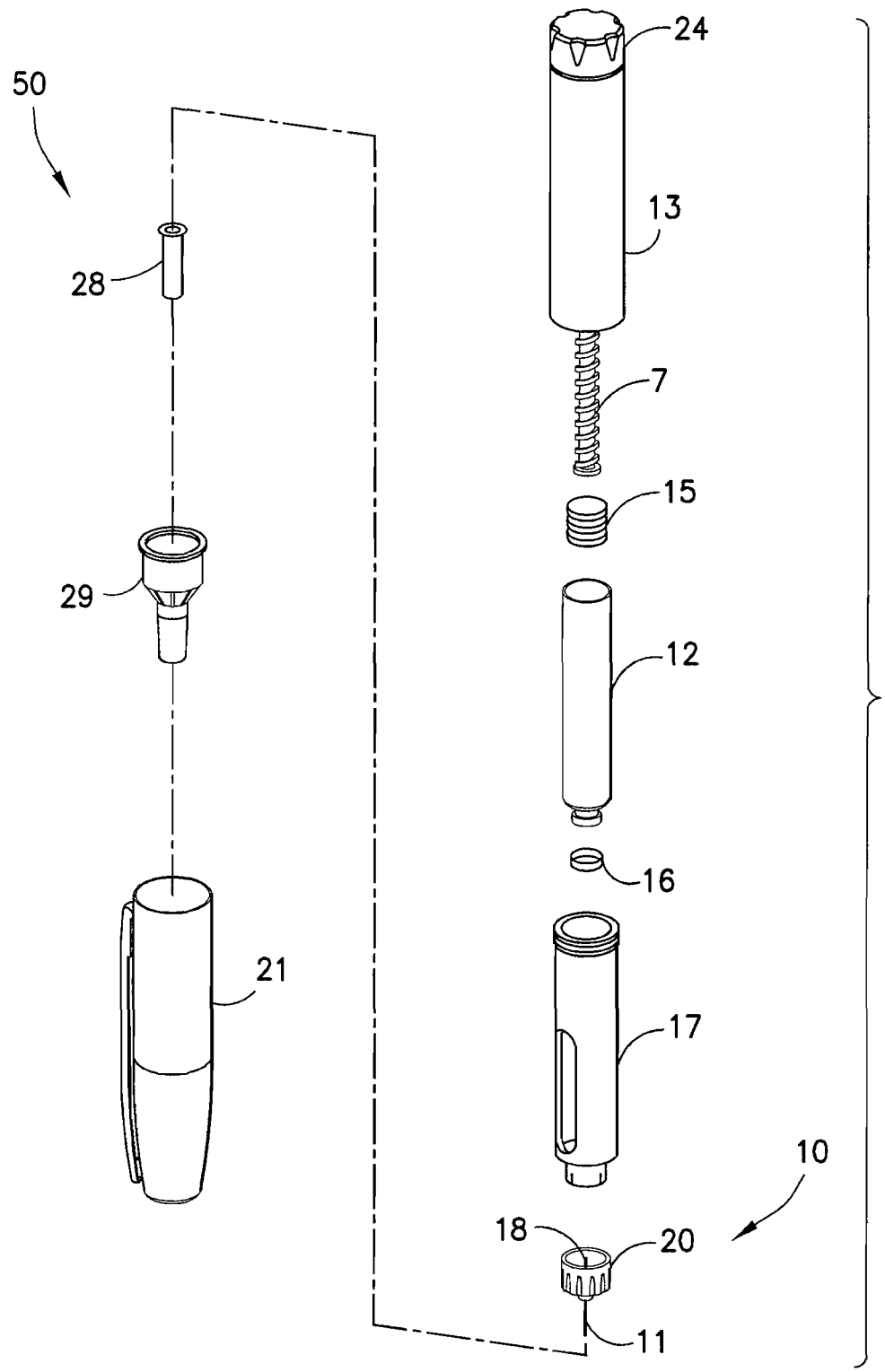
FIG. 2 is an exploded view of the exemplary drug delivery pen of FIG. 1.
Figure 3:
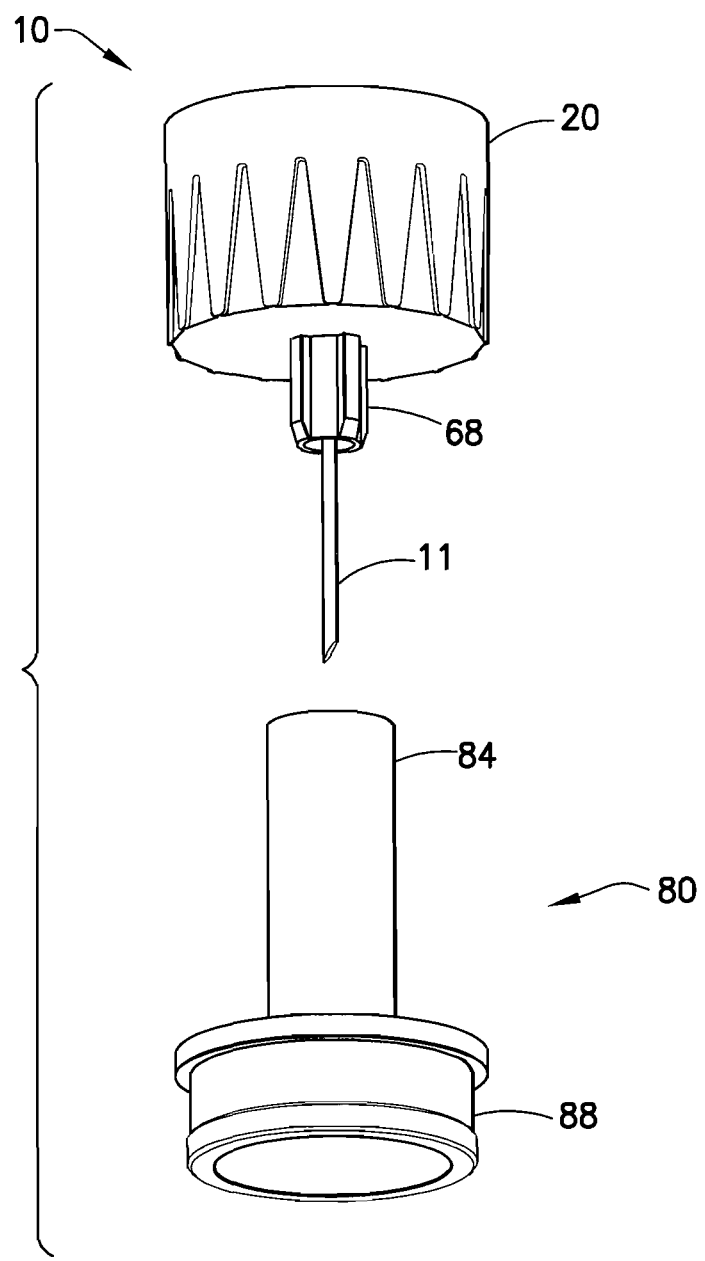
FIG. 3 is a perspective view of a pen needle and a needle cover in accordance with an embodiment of the present invention.

FIG. 3 is a perspective view of the pen needle 10 and a needle cover unit or cover 80 in accordance with an embodiment of the present invention. The cover 80 replaces the inner shield of FIG. 2 in addition to other functions, as will be described in greater detail below. As shown in FIG. 3, the needle 10 includes the hub 20 disposed at a non-patient end thereof. A protrusion 68 extends from a patient end of the hub 20 and the patient needle 11 extends from the protrusion 68. The septum-penetrating needle cannula 18 (best shown in FIG. 5) disposed within the non-patient end of the hub 20 fluidly communicates with the patient needle 11.

Figure 4:
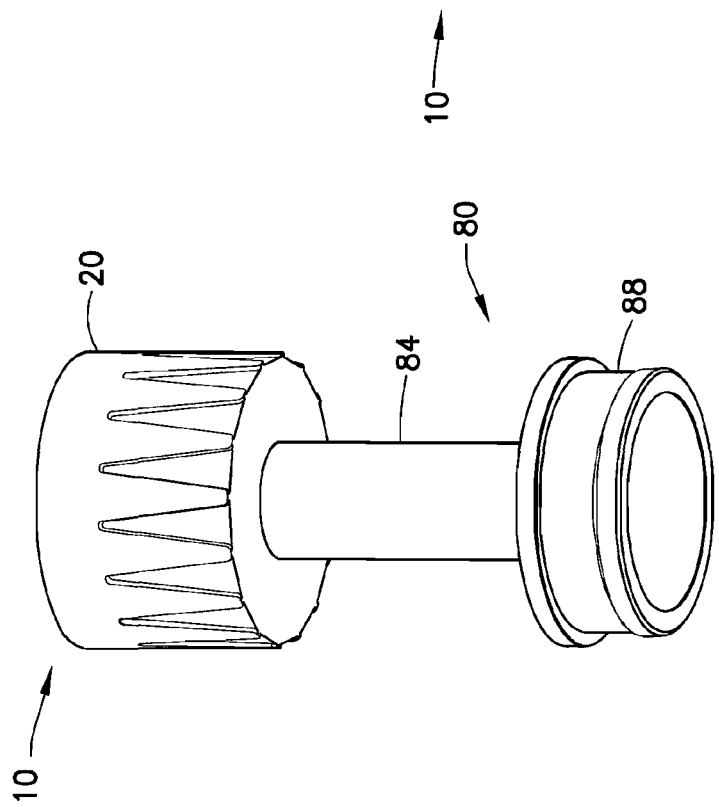
FIG. 4 is a perspective view of the pen needle and needle cover of FIG. 3 engaged to cover a patient end of the pen needle.

The cover 80 includes a needle-covering portion 84 and a hub-covering portion 88, as shown in FIG. 3. Thus, in this embodiment, the needle-covering portion 84 and the hub-covering portion 88 are coupled because they are integrally formed as a unitary structure. The shape of the interior of the needle-covering portion 84 (best seen in FIG. 5) corresponds to the shape of the protrusion 68 to facilitate connection between the cover 80 and the pen needle 10. More specifically, in a first orientation of the cover 80 relative to the pen needle 10, the needle-covering portion 84 fits over and connects to the protrusion 68 to cover the patient needle 11, as shown in FIG. 4. The connection between the protrusion 68 and the needle-covering portion 84 may be, for example, an interference fit or a snap fit.

Figure 5:
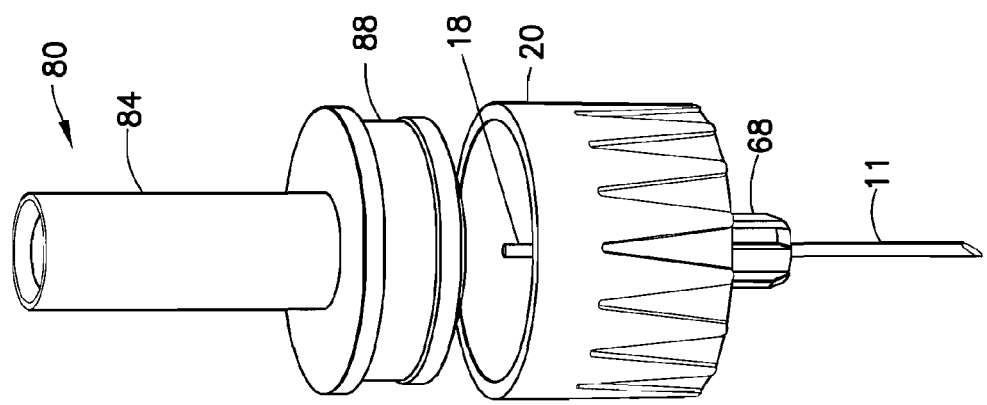
FIG. 5 is a perspective view of the pen needle and needle cover of FIG. 3 illustrating an arrangement to cover a non-patient end of the pen needle.

Similar to the connection between the protrusion 68 and the needle-covering portion 84, as shown in FIG. 5, the external shape of the hub-covering portion 88 corresponds to the interior shape of the hub 20 to facilitate connection between the cover 80 and the pen needle 10. More specifically, as shown in FIG. 6, in a second orientation of the cover 80 relative to the pen needle 10, the hub-covering portion 88 fits within and connects to the non-patient end of the hub 20 to cover the hub 20 and the septum-penetrating needle cannula 18. The connection between the hub-covering portion 88 and the hub 20 may be, for example, an interference fit or a snap fit.

A sterility barrier is formed on the non-patient end of the pen needle 10 by the hub-covering portion 88 of the cover 80 being securely connected to the hub 20 on the non-patient side of the pen needle. Similarly, a sterility barrier for the patient end of the pen needle 10 is the needle-covering portion 84, which acts as an inner shield on the patient needle 11 and fits onto the protrusion 68 of the hub 20. The sterility barrier for both ends of the pen needle 10 preferably involves a tortuous path.

A tortuous path closure can be defined as a barrier to airborne microorganisms, accomplished by creating a convoluted pathway to the product (for example, a labyrinth path or a screw-threaded closure). A tortuous path is neither airtight nor watertight. It provides a barrier to ingress by microorganisms but not by fluids. Louis Pasteur, in 1861, discovered the principle of tortuous path closures. He determined that a sterilized glass flask with a swan-shaped tortuous neck, even with the end open, would remain sterile.

When microorganisms are out of liquid, they cannot move on their own and cannot turn corners. Rather, most microbes float in the air, often on dust particles. These dust-riding microbes have mass and momentum and settle by gravity. They also have static charges and are attracted to surfaces by intramolecular and electrostatic forces. Another mechanism of particle movement is Brownian motion. This random motion of particles in static airflow also causes microorganisms to impact surfaces.

With a tortuous path or labyrinth enclosure, air pressure changes cause air to move in and out of the enclosed volume. While the air moves around the turns, the organisms impact surfaces, causing them to be "filtered" out of the air. With the low air velocities caused by normal environmental pressure changes, the bacteria tend to stay where they have landed. The sterility barriers of these tortuous path closure systems are created by the repeated turns microorganisms would have to make to breach product sterility. The small air volume in many tortuous path products also helps by reducing the air volume that is exchanged with the atmosphere.

Figure 7:
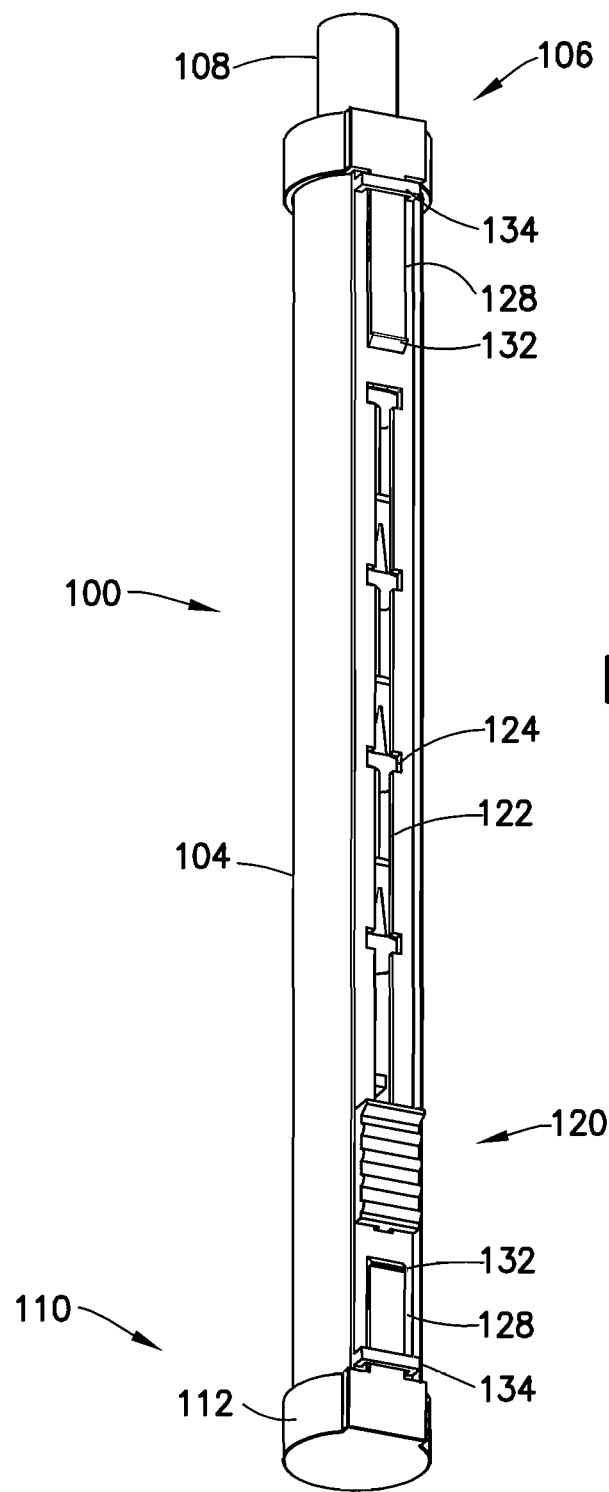
FIG. 7 is a perspective view of a case in accordance with an embodiment of the present invention.

FIG. 7 is a perspective view of a needle dispensing and storing case 100 in accordance with an embodiment of the present invention. As shown in FIG. 7, the case 100 includes a main body or tube 104, a dispensing end cap 108, a storage end cap 112, and an advancing member or clicker 120. The tube 104 includes a slot 122 in which the clicker 120 moves, and a plurality of detents 124 to provide positive stops for the clicker 120 at discrete points along the slot 122. The dispensing end cap 108 is disposed at a dispensing end 106 of the tube 104 and selectively covers the dispensing end 106. Similarly, the storage end cap 112 is disposed at a storage end 110 of the tube 104 and selectively covers the storage end 110. In other words, tube 104 has two ends: the dispensing end 106, where unused pen needles are accessed for use; and the opposing storage end 110, which has a space for the pen needles 10 to be stored after use. Each end has a cover 108 and 112 to avoid inadvertent access to the pen needles 10. As described in greater detail below, these covers 108 and 112 are attached to the tube 104 in such a way that they can be partially removed to access the pen needles 10 but can still be retained with the tube 104.

As shown in FIG. 7, each of the end caps 108 and 112 has at least one cap leg 128 with a cap foot 132 disposed at a distal end thereof. Correspondingly, each of the dispensing and storage ends of the tube 104 includes at least one cap-retaining structure 134. The cap portions of the end caps 108 and 112 are hingedly connected to their respective cap legs 128 by, as a non-limiting example, a living hinge.

To secure an end cap (108 or 112) to an end of the tube 104, a user slides the cap foot 132 and the cap leg 128 through the cap-retaining structure 134. When a user disengages the dispensing end cap 108 and/or the storage end cap 112 from their respective ends, the raised cap foot 132, in conjunction with the cap-retaining structure 136, keeps the cap 108 and/or 112 connected to the tube 104 while providing access to the respective ends. In addition, according to one embodiment, respective bases of the end caps 108 and 112 have shapes corresponding to ends of the tube 104, and provide, for example, an interference fit or a snap fit.

According to another embodiment (best shown in FIGS. 14-16), the dispensing end cap 108 and the storage end cap 112 are hingedly connected to the tube 104. A living hinge can be used to connect the dispensing end cap 108 and the storage end cap 112 to the tube 104.

Figure 9:
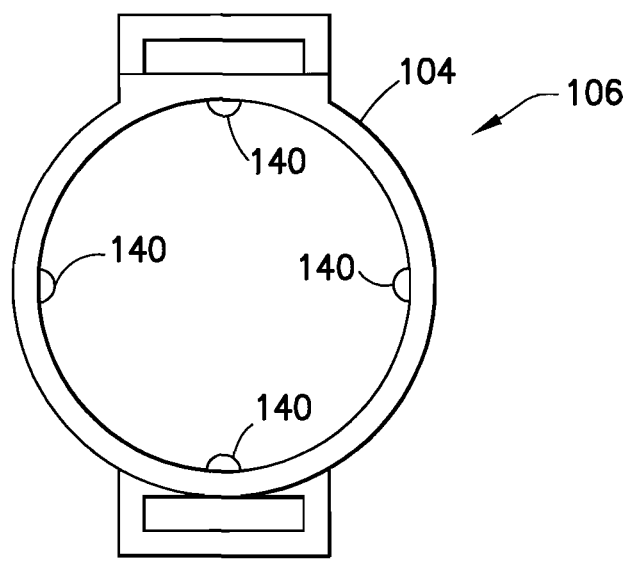
FIG. 9 is an end view of the dispensing end of the case of FIG. 7.

FIG. 8 is a perspective view of the dispensing end 106 of the case 104 and FIG. 9 is an end view of the dispensing end 106 of the case 104. As illustrated in FIGS. 8 and 9, the dispensing end 106 of the case 104 includes a plurality of anti-rotation/retaining structures 140. At the dispensing end 106 of the case 104, the anti-rotation/retaining structures 140 work in conjunction with the hub 20 of a pen needle 10 to prevent rotation of the pen needle 10 when the pen needle 10 is in a dispensing position. For example, when the pen needle 10 is in the dispensing position and the anti-rotation/retaining structures 140 are engaged with the hub 20, the anti-rotation/retaining structures 140 prevent the pen needle 10 from rotating and permit the user to connect a pen injector 50 (or a medicament cartridge 12) to the hub 20 by threading the pen injector 50 (or medicament cartridge 12) into the hub 20. While preventing rotation of the pen needle 10 during connection to the pen injector 50, subsequent to the connection, the fit between the anti-rotation/retaining structures 140 and the pen needle 10 permits the user to axially withdraw the combined pen injector 50 and pen needle 10 from the tube 104.

Though not illustrated, anti-rotation/retaining structures 140 are similarly disposed at the storage end 110 of the tube 104 to facilitate disconnection between the pen injector 50 and the pen needle 10, and also facilitate storage of the used pen needles 10 in the storage end 110 of the tube 104. For example, as discussed in greater detail below, once the hub 20 of a given pen needle 10 is inserted into the storage end 110 of the tube 104 past the anti-rotation/retaining structures 140, the structures 140 act as a barrier to prevent easy removal of the used pen needle 10 from the storage end 110 of the tube 104.

Figure 10:
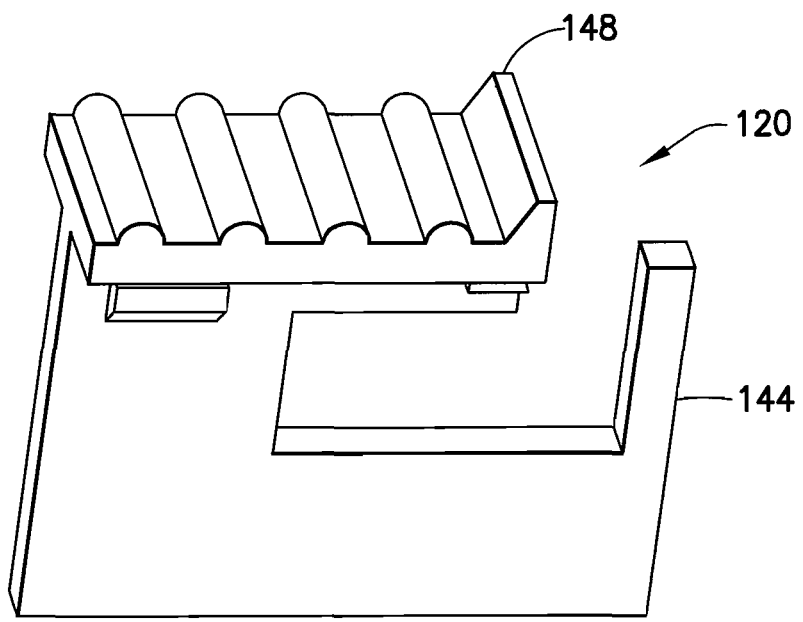
FIG. 10 is a perspective view of an advancing member of the case of FIG. 7.
Figure 11:
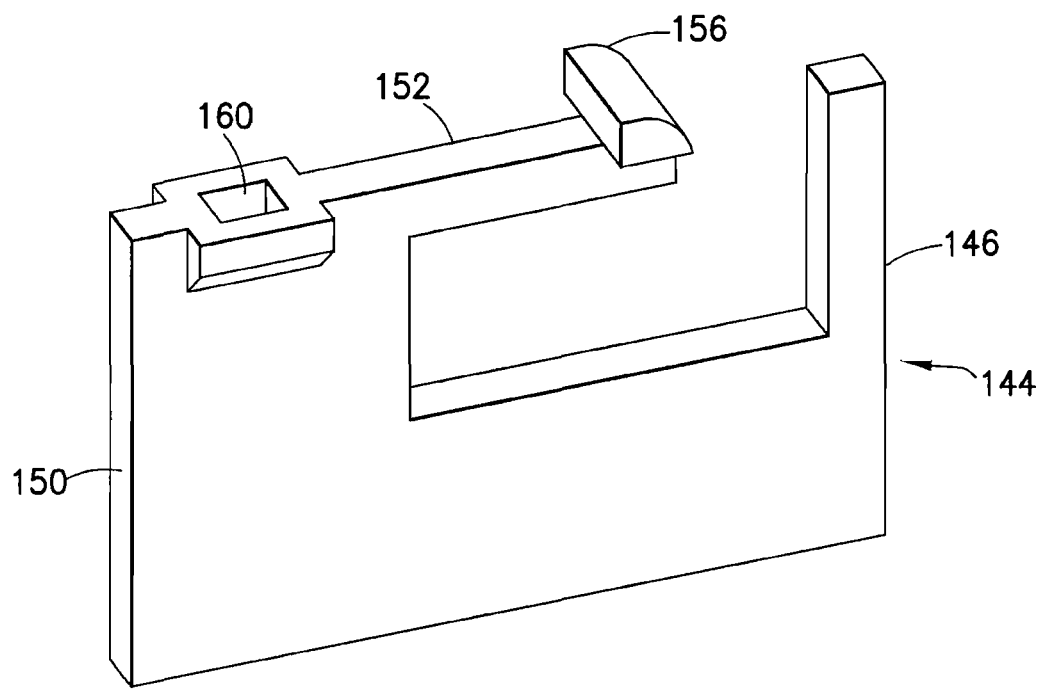
FIG. 11 is a perspective view of a pusher of the advancing member of FIG. 10.
Figure 12:
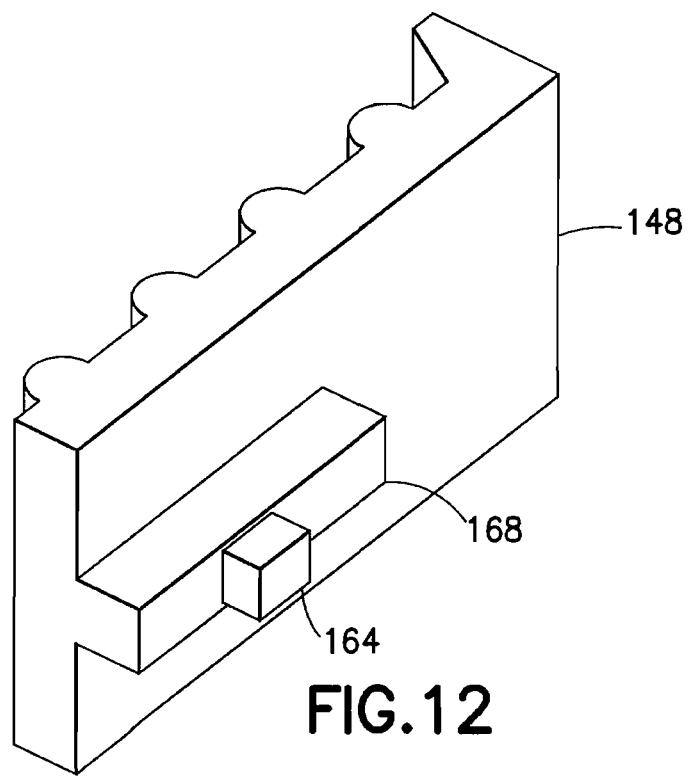
FIG. 12 is a perspective view of the bottom of a pusher top of the advancing member of FIG. 10.

FIGS. 10 to 12 illustrate the advancing member or clicker 120 in accordance with an embodiment of the present invention. As shown in FIG. 10, the clicker 120 includes a pusher 144 and a pusher top 148. In general, a pusher 144 is disposed within the tube 104 and the pusher top 148 is disposed outside the tube 104. As will be discussed in greater detail below, the user actuates the pusher top 148 to move unused needles toward the dispensing end 106 of the tube 104.

The pusher 144 has a dispensing end 146 and a storage end 150. As FIG. 11 also illustrates, the pusher 144 includes a cantilevered arm 152 extending from a top portion thereof, and the cantilevered arm 152 includes a detent-engaging member 156 disposed at a distal end thereof. In use, the detent-engaging member 156 individually engages the detents 124 to provide positive stops for the clicker 120 as the clicker 120 moves along the slot 122. Additionally, the pusher 144 includes an engaging portion 160 to facilitate coupling of the pusher top 148 with the pusher 144. Correspondingly, as shown in FIG. 12, the pusher top 148 includes an engagement protrusion 164 extending from a guide 168. The engagement protrusion 164 engages the engaging portion 162 to couple the pusher top 148 and the pusher 144. Further, the guide 168 rides in the slot 122 to guide the clicker 120 along the tube 104 and prevent rotation of the pusher top 148 relative to the tube 104.

Figure 13:
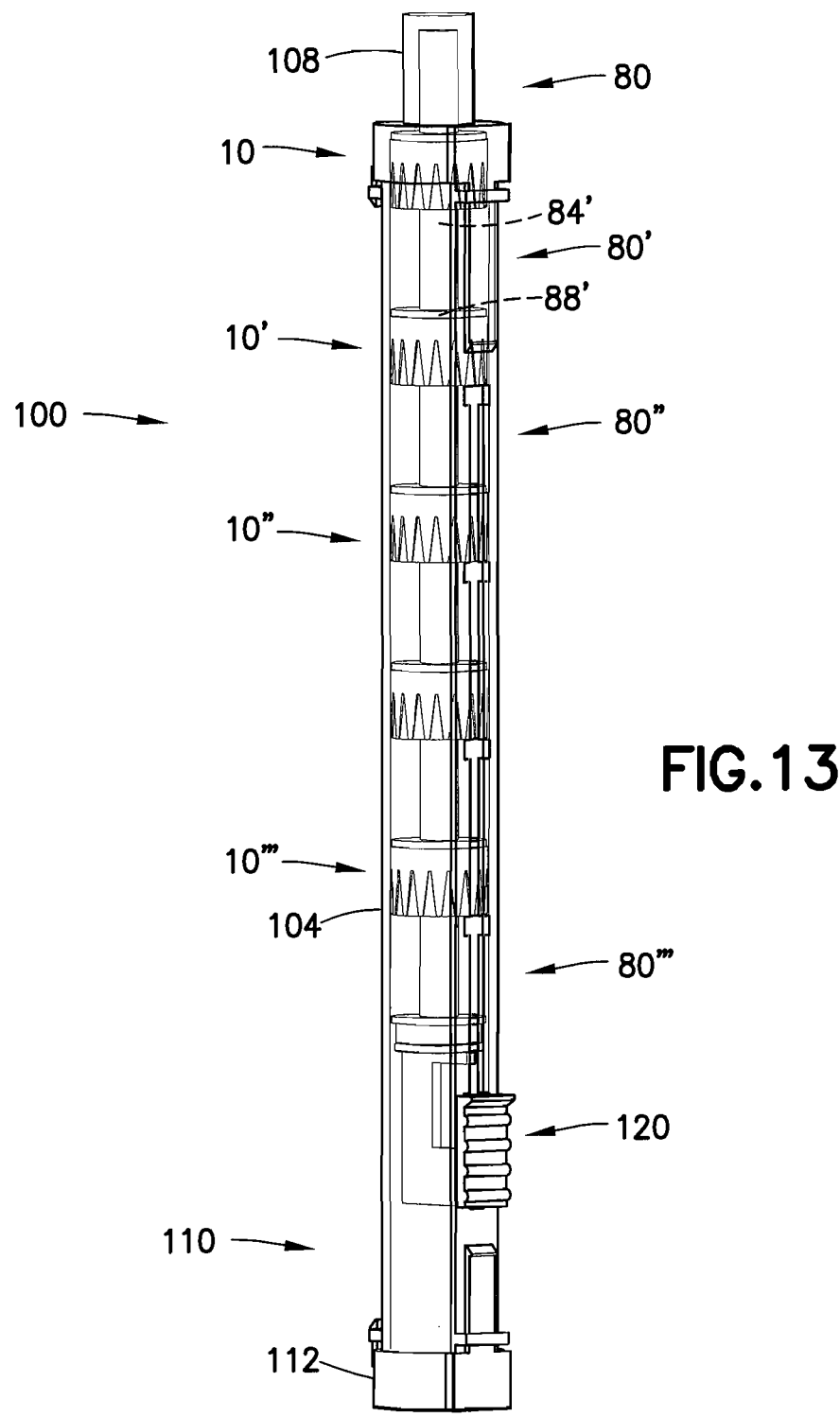
FIG. 13 is a perspective view of the case of FIG. 7 and a plurality of pen needles and needle covers of FIG. 3 in accordance with an embodiment of the present invention.

FIG. 13 is a perspective view of the case 100 and a plurality of pen needles 10 and needle covers 80 in accordance with an embodiment of the present invention. FIGS. 14-17 are perspective views illustrating operation of the needle dispensing and storing case 100. In FIGS. 7-9, the tube 104, the dispensing end cap 108, and the storage end cap 112 are shown as being opaque. But for illustrative purposes, in FIGS. 13-17, the tube 104, the dispensing end cap 108, and the storage end cap 112 are shown as being translucent. As one of ordinary skill in the art will appreciate, the tube, the dispensing end cap, and the storage end cap may be translucent, transparent, or opaque without departing from the scope of the invention.

As shown in FIG. 13, a first pen needle 10 disposed at the dispensing end 106 of the tube 104 in the dispensing position has a first cover 80 connected to the hub 20 and covering the non-patient end of the pen needle 10. Additionally, the patient end of the first pen needle 10 connects to the needle-covering portion 84' of a second cover 80'. Likewise, the second cover 80' also connects to a second pen needle 10' via the hub-covering portion 88'. Moreover, a third cover 80" connects both to the second pen needle 10' and a third pen needle 10". Needle covers 80 and pen needles 10 are similarly connected until a final cover 80''' that is adjacent to the clicker 120 connects only to a single pen needle 10'''. In other words, the cover 80 covering the patient end of one pen needle 10 also fits into a mating feature on the hub 20 of the non-patient end of the next pen needle 10.

To use the needle dispensing and storing case 100, the user ensures that a pen needle 10 is in the dispensing position by moving the clicker toward the dispensing end 106 of the tube 104. Put differently, because the clicker 120 is adjacent to and contacts the final cover 80''', advancing the clicker 120 toward the dispensing end 106 of the tube 104 advances all needles 10 and needle covers 80 on the dispensing end 146 of the pusher 144 toward the dispensing end 106 of the tube 104. During use, as the user advances the clicker 120 toward the dispensing end 106 of the tube 104, the detent engaging member 156 clicks into a detent 124 as each successive cover 80 and pen needle 10 reaches the dispensing position.

Figure 14:
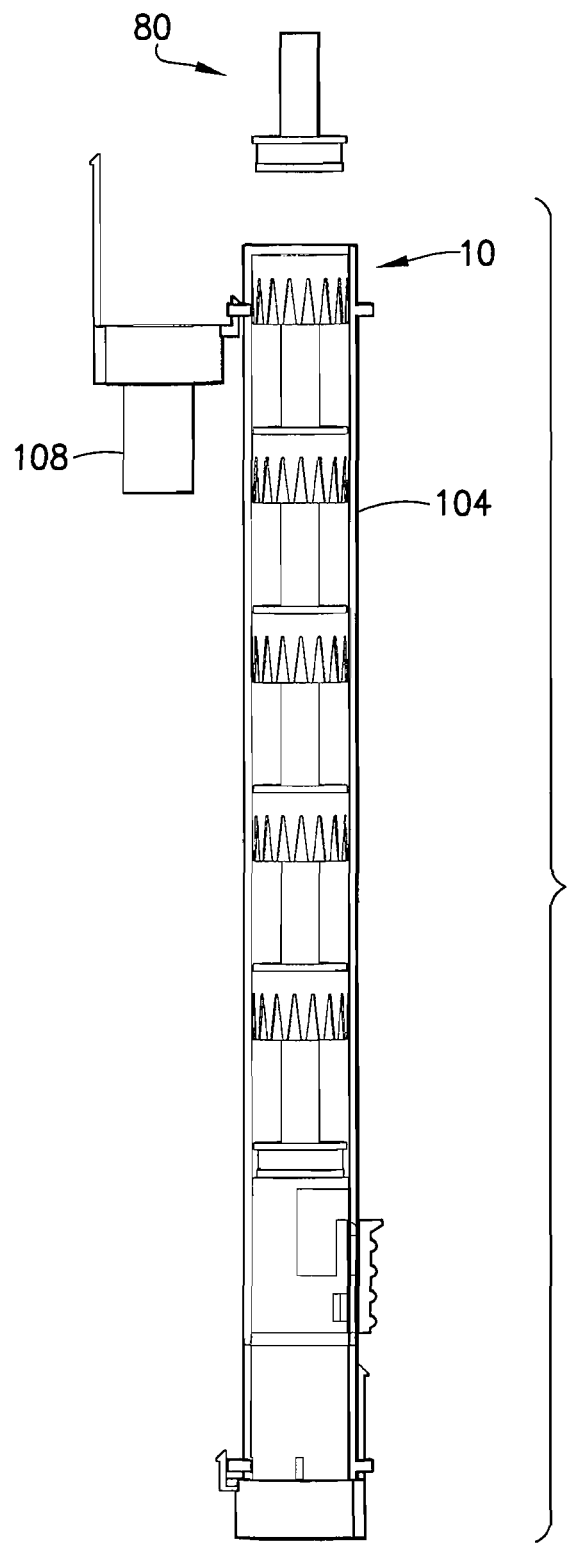
FIGS. 14-17 are perspective views illustrating operation of the case of FIG. 7.
Figure 15:
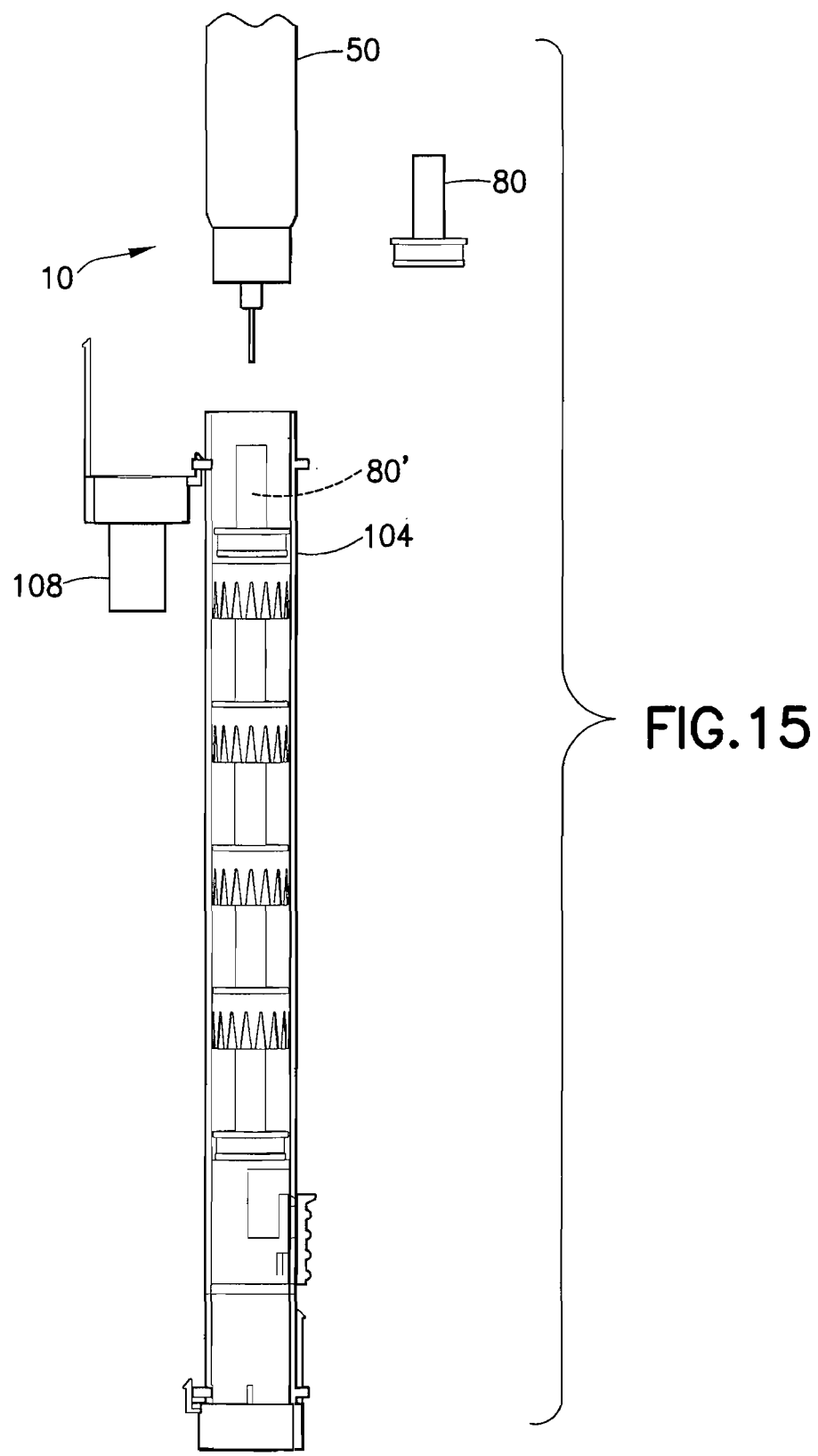

Subsequently, as shown in FIG. 14, the user opens the dispensing end cap 108 and removes the cover 80, thereby exposing the non-patient end of the pen needle 10. Next, the user connects a pen injector (for example, 50) to the non-patient end of the pen needle 10 and removes the pen needle 10 from connection with the cover 80' and from the tube 104, as shown in FIG. 15.

Figure 16:
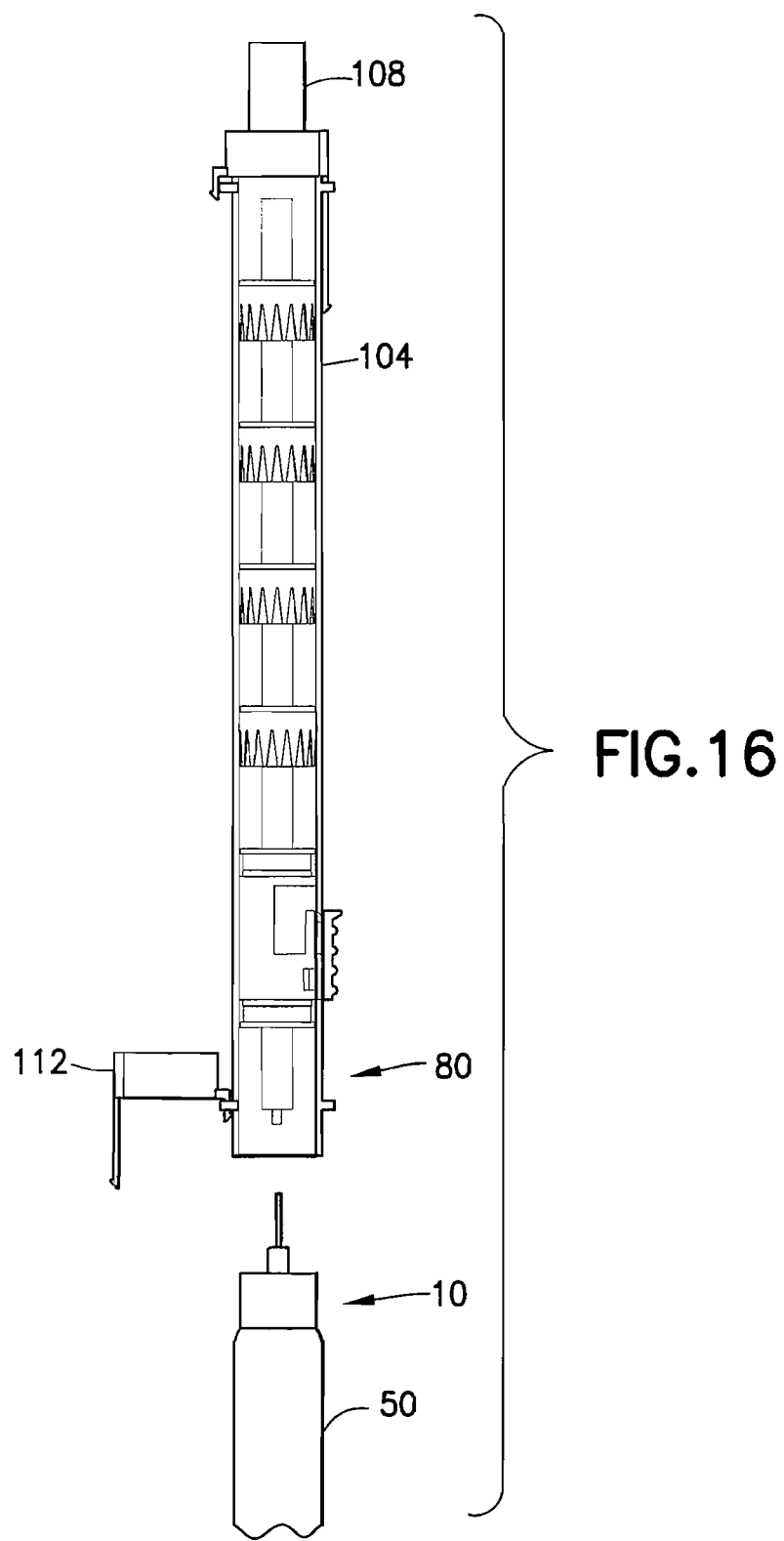
Figure 17:
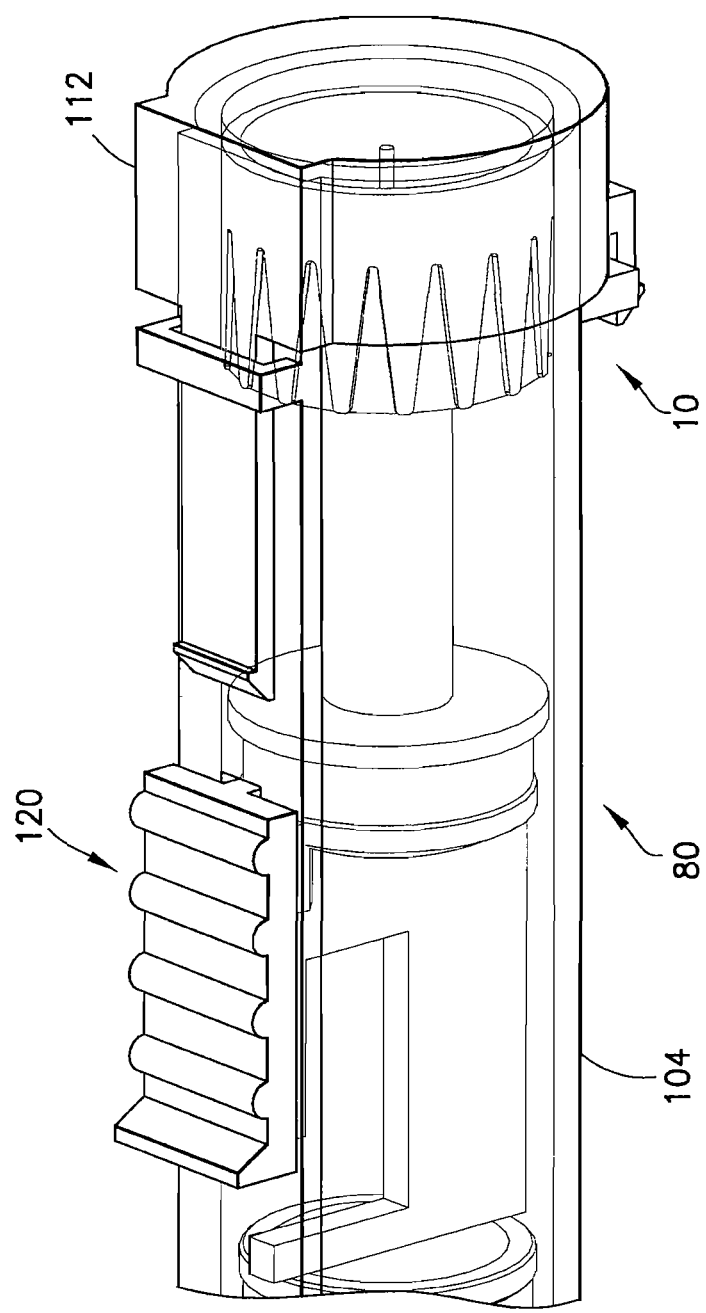

After performing the injection and closing the dispensing end cap 108, the user opens the storage end cap 112 to store the used pen needle 10, as shown in FIG. 16. Optionally, the user may insert the cover 80 into the storage end 110 of the tube 104, with the hub-covering portion 88 toward the dispensing end 106 of the tube 104. According to one embodiment, the hub-covering portion 88 of the cover 80 is connectable to the storage end 150 of the pusher 144. Next, the user inserts the pen needle 10 into the storage end 110 of the tube 104 to engage the needle-covering portion 84 of the cover 80 with the anti-rotation/retaining structures 140, and unscrews the pen injector from the pen needle 10. Subsequently, as shown in FIG. 17, the user closes the storage end cap 112. For further use, the clicker 120 is moved into the next detent position to push the next unused pen needle (for example, 10') into the dispensing position. According to one embodiment, the user engages the needle-covering portion 84 to the pen needle 10 prior to inserting the engaged assembly into the storage end 110 of the tube 104, to engage the hub 20 with the anti-rotation/retaining structures 140.

As additional pen needles 10 are used, they can be inserted into the storage end 110 of the tube 104, pushing previously stored used pen needles 10 further into the tube 104 in the space created by moving the clicker 120 toward the dispensing end 106 of the tube 104. Thus, in addition to moving unused pen needles 10, the clicker 120 serves as a separator between used and unused pen needles 10. As the clicker 120 is advanced to a detent 124, the position of the clicker 120 also serves as a visual indicator as to how many unused pen needles remain in the tube 104.

According to one embodiment, as shown, for example, in FIG. 13, prior to the removal of the first cover 80, the tube 104 has a space at the storage end 110 thereof to receive a needle cover and/or a pen needle. According to another embodiment, initially, there is no such space at the storage end 110 of the tube 104, and storage space for a used needle cover and/or pen needle is created within the tube 104 by moving the clicker 120 toward the dispensing end 106 of the tube 104.

One advantage of embodiments of the present invention is that labels are not needed on the hub 20 of a pen needle 10 to provide a sterility barrier. This function is provided by an adjacent cover 80. Put another way, a cover 80 provides a sterility barrier to the patient needle 11 of one pen needle 10 and also provides a sterility barrier to the hub 20 of an adjacent pen needle 10 because the cover 80 is connected to patient end of the one pen needle 10 and is also connected to the hub 20 of the adjacent pen needle 10.

Figure 18:
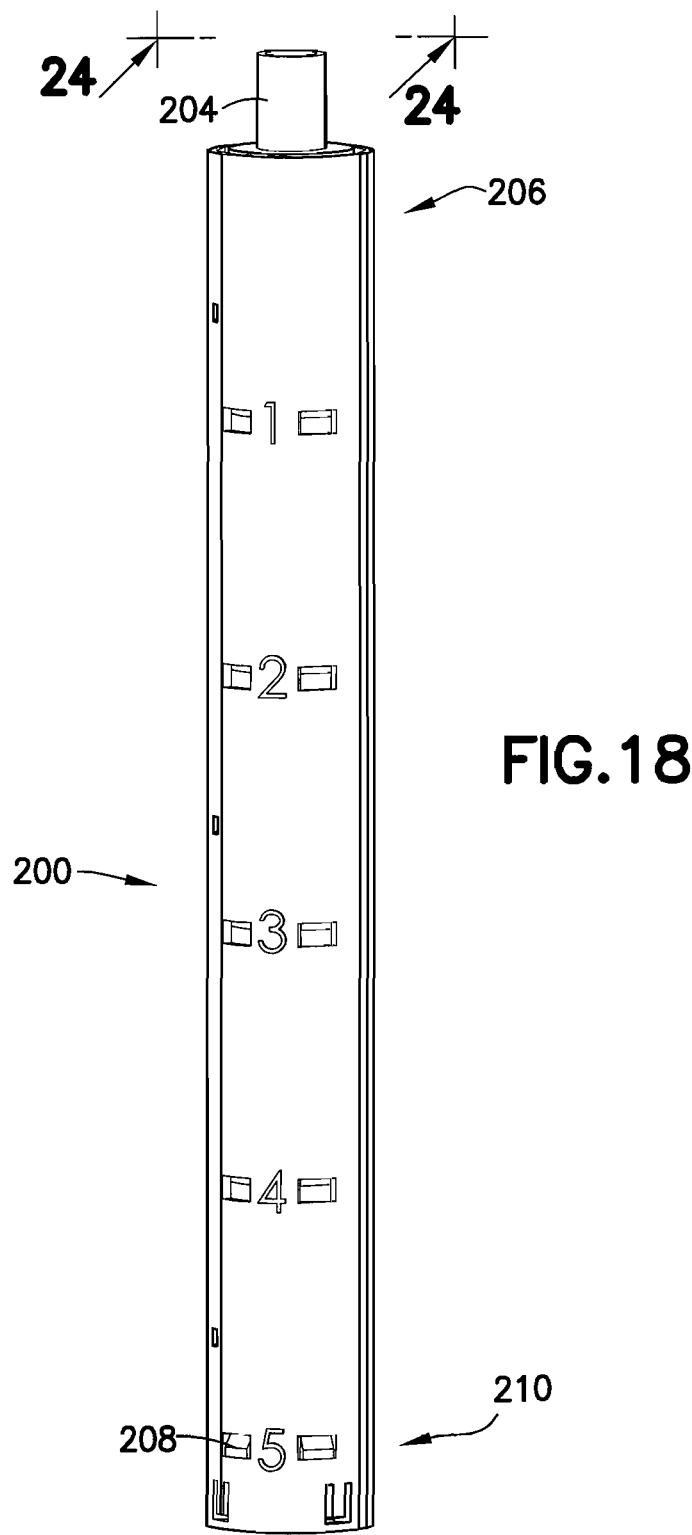
FIG. 18 is a perspective view of a case in accordance with another embodiment of the present invention.

FIG. 18 is a perspective view of a case 200 in accordance with another embodiment of the present invention. The case 200 has a dispensing end 206 for dispensing pen needles and a storage end 210 for storing used pen needles. As shown in FIG. 18, a hub cover 204 is disposed at the dispensing end 206 of the case 200. Additionally, as will be described in greater detail below, toward the storage end 210 of the case 200, a separator 208 indicates the number of remaining pen needles within the case 200.

Figure 19:
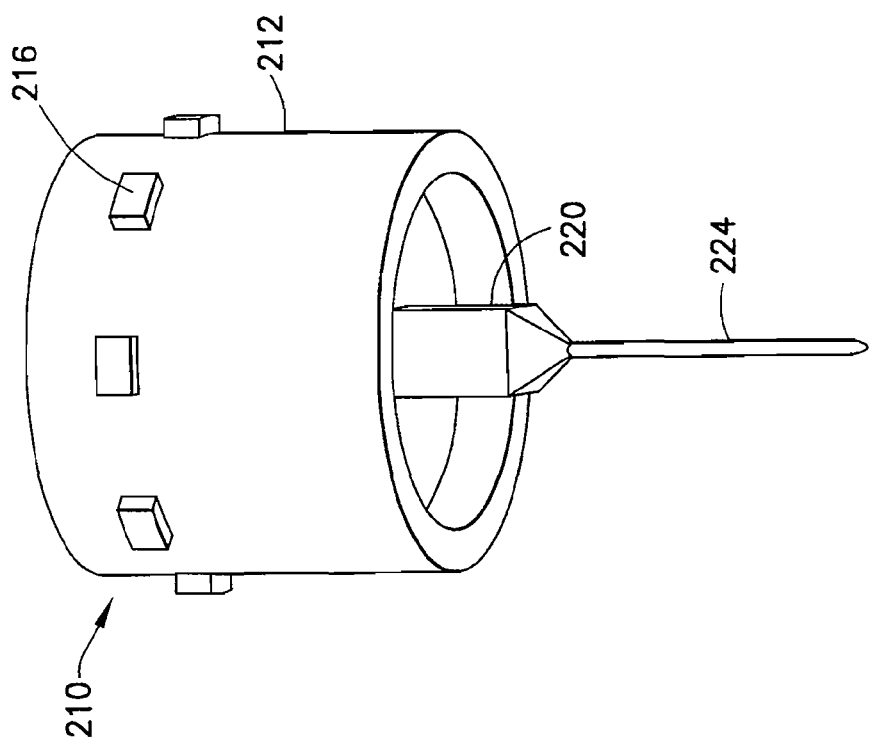
FIG. 19 is a perspective view of a pen needle in accordance with an embodiment of the present invention.

FIG. 19 is a perspective view of a pen needle 210 in accordance with an embodiment of the present invention. As shown in FIG. 19, the pen needle 210 includes a hub 212 with a plurality of bosses 216 extending radially therefrom. Additionally, a protrusion 220 extends axially from a patient end of the hub 212, and the patient needle 224 extends axially from the protrusion 220. Similar to the pen needle 10 described above, a septum-penetrating needle cannula 228 (best shown in FIG. 21) extends axially within the hub 212 on a non-patient end of the hub 212. The needle cannula 228 is in fluid communication with the patient needle 224.

Figure 20:
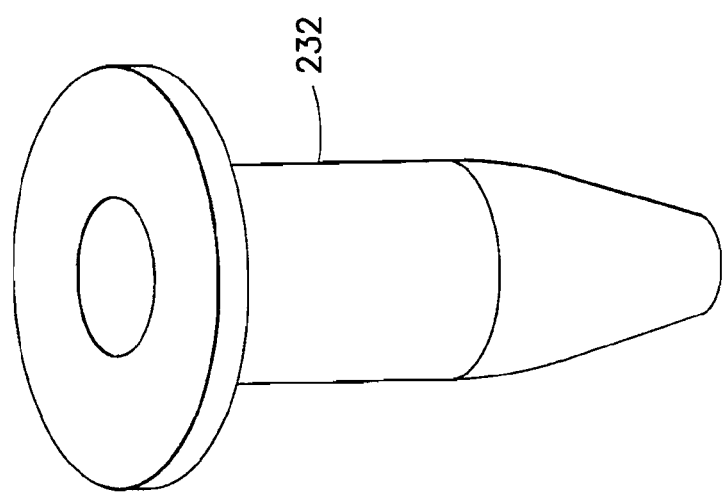
FIG. 20 is a perspective view of a needle cover in accordance with an embodiment of the present invention.
Figure 21:
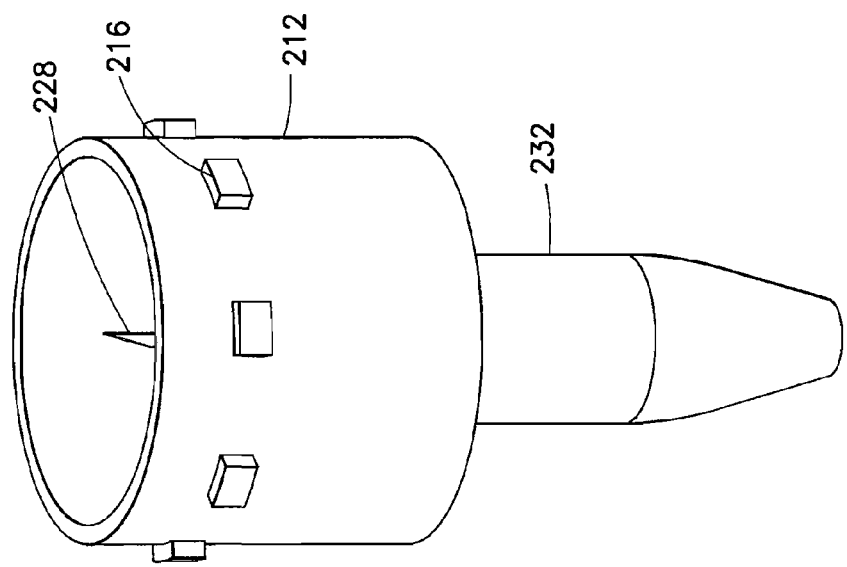
FIG. 21 is a perspective view of a combination of the pen needle of FIG. 19 and the needle cover of FIG. 20.

FIG. 20 is a perspective view of a needle cover 232 in accordance with an embodiment of the present invention. As shown in FIG. 21, the needle cover 232 selectively engages the protrusion 220 of the pen needle 210 to protect the patient needle 224 and provide a sterility barrier therefor.

Figure 22:
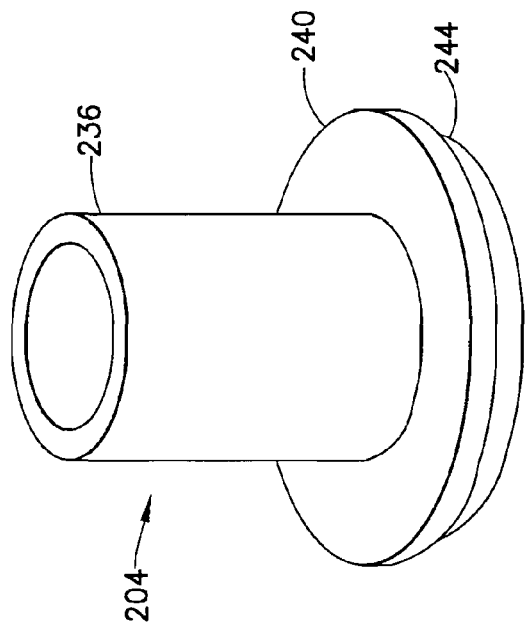
FIG. 22 is a perspective view of a hub cover in accordance with an embodiment of the present invention.

FIG. 22 is a perspective view of the hub cover 204. As shown in FIG. 22, the hub cover 204 includes a needle cover receiving portion 236 and a hub-covering portion 240. The hub-covering portion 240 includes an insertion portion 244. As described in greater detail below, the needle cover receiving portion 236 selectively receives a needle cover 232. In addition, the non-patient end of the hub 212 receives the insertion portion 244 of the hub-covering portion 240 to protect the septum-penetrating needle cannula 228 and provide a sterility barrier therefor.

According to one embodiment, the interface between the needle cover 232 and the protrusion 220 and the interface between the hub cover 204 and the non-patient end of the hub 212 are form-fit or interference-fit tortuous paths, thereby providing the respective sterility barriers.

Figure 23:
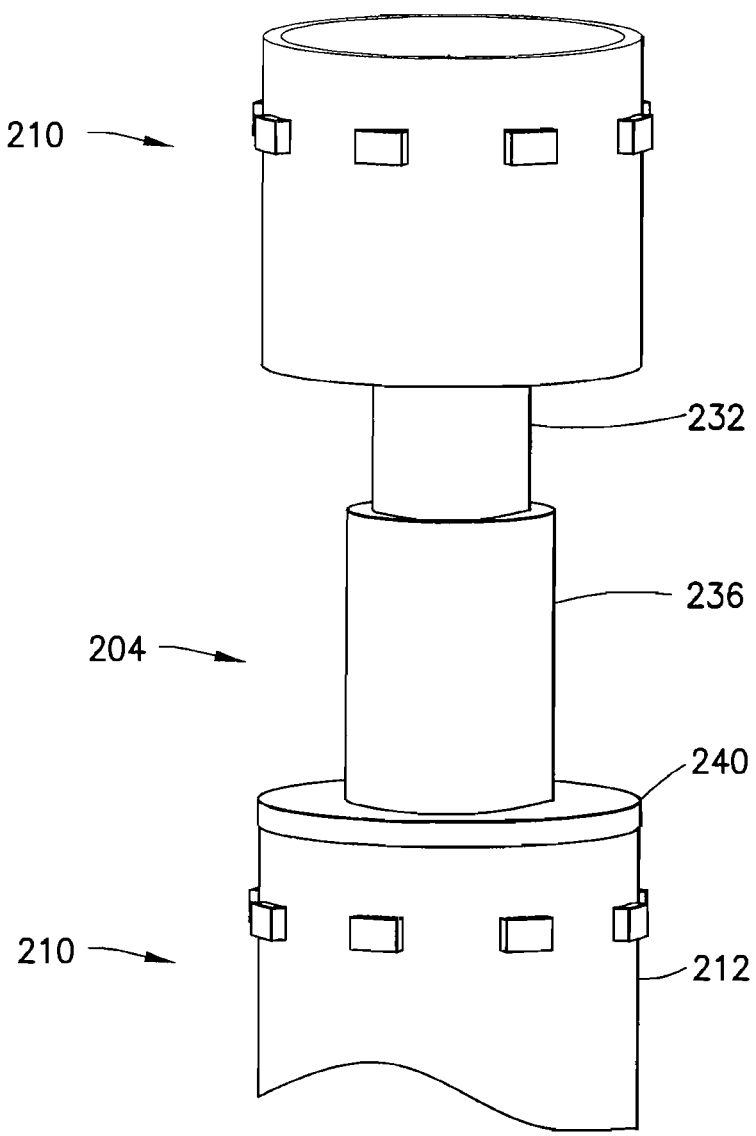
FIG. 23 is a perspective view of a combination of the pen needle of FIG. 19, the needle cover of FIG. 20, the hub cover of FIG. 22, and another pen needle of FIG. 19.

FIG. 23 is a perspective view of a combination of the pen needle 210, the needle cover 232, the hub cover 204, and another pen needle 210. Collectively, the needle cover 232 and the hub cover 204 form a needle cover unit or cover having a needle-covering portion and a hub-covering portion. As shown in FIG. 23, the upper pen needle 210 engages the needle cover 232. In turn, the needle cover receiving portion 236 of the hub cover 204 receives the needle cover 232, thus coupling the needle cover 232 and the hub cover 204. Further, the non-patient end of the hub 212 of the lower pen needle 210 receives the insertion portion 244 of the hub-covering portion 240 of the hub cover 204. In this way, a plurality of pen needles 210, needle covers 232, and hub covers 204 can be connected together in a sterile manner.

Figure 24:
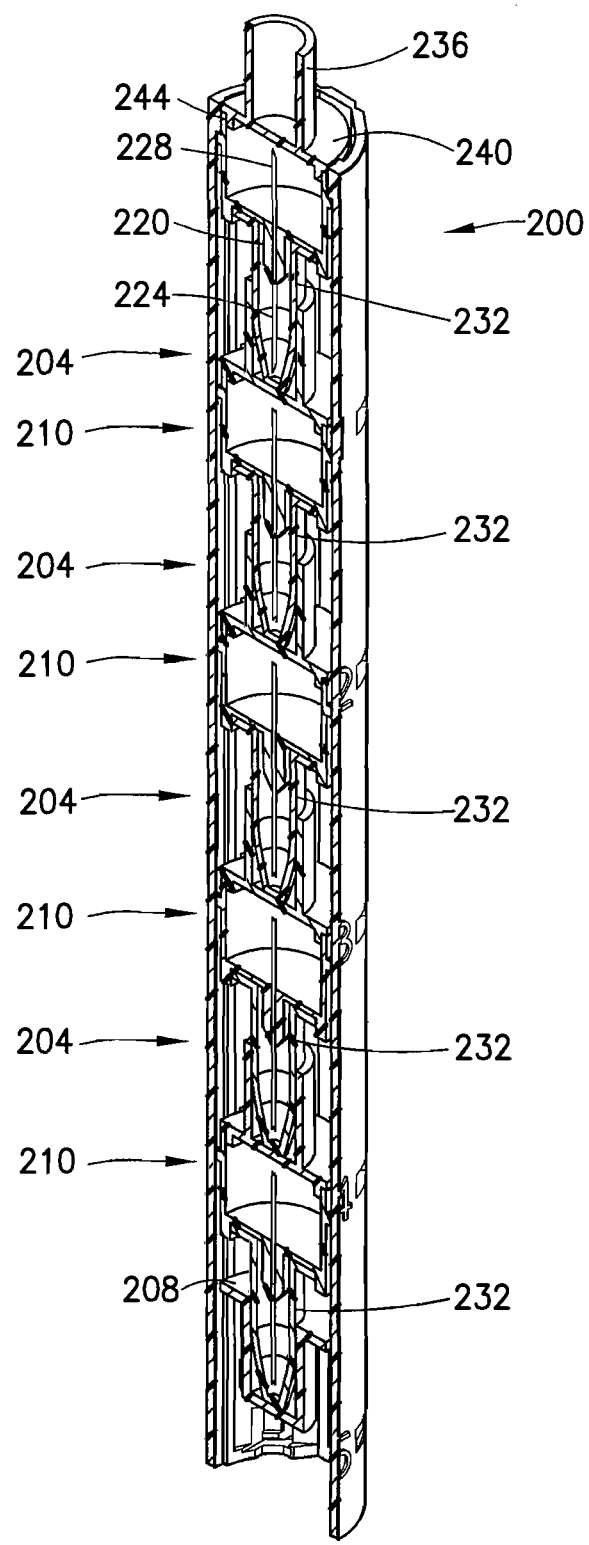
FIG. 24 is a perspective view in cross-section of the case of FIG. 18 taken along line 24-24 in FIG. 18.

According to one embodiment, the plurality of pen needles 210, needle covers 232, and hub covers 204 are connected in the above-described sterile manner and stored within the case 200, as shown in FIG. 24. FIG. 24 is a perspective view in cross-section of the case 200 taken along line 24-24 in FIG. 18. In such a configuration, when the case 200 is full of unused pen needles 210, a separator 208 is disposed toward the storage end 210 of the case 200.

FIG. 25 is a perspective view of the separator 208. As shown in FIG. 25 the separator 208 includes a needle cover receiving portion 248 and an indicator portion 252 that includes a plurality of cantilevered legs 256, each having a marker or indicator 260 disposed at a free end thereof. As described in greater detail below, the indicator 260 indicates the number of unused pen needles 210 remaining in the case 200.

Figure 27:
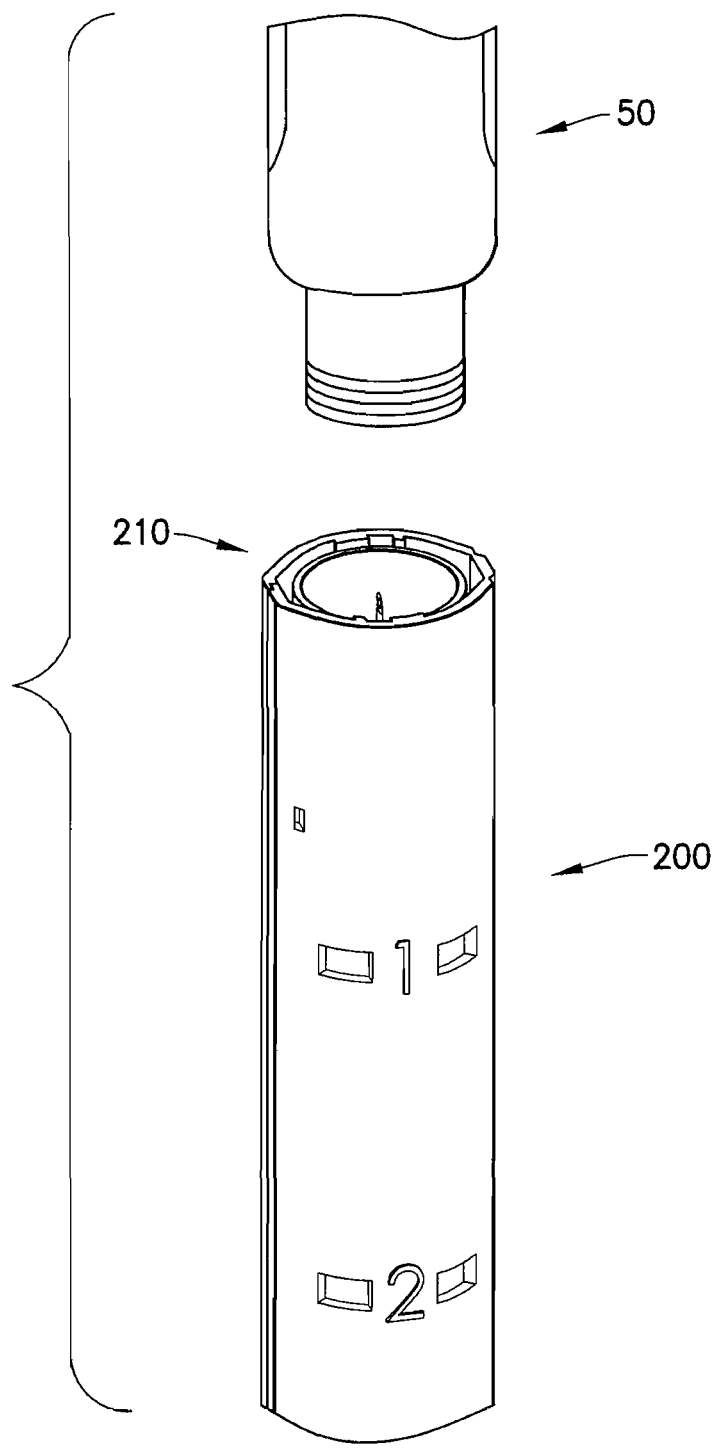
FIG. 27 is a partial perspective view of the case of FIG. 18 and a pen injector.

To use the case 200, as shown in FIG. 26, the user first removes the hub cover 204 from the pen needle 210 disposed at the dispensing end 206 of the case 200 in a dispensing position. Next, as shown in FIGS. 27 and 28, the user connects a pen injector (for example, pen injector 50) to the pen needle 210 in the dispensing position.

Figure 28:
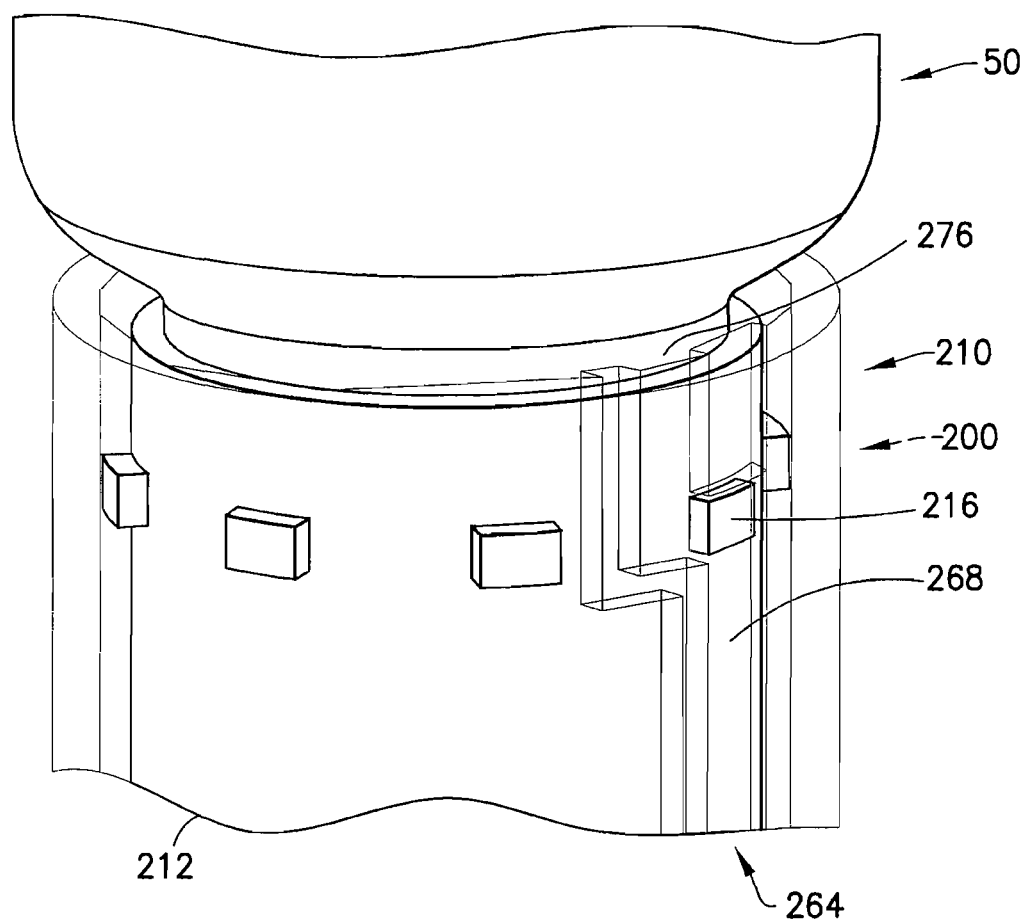
FIG. 28 is a partial perspective view of the pen injector of FIG. 27 connected with a pen needle of FIG. 19 within the case of FIG. 18.

FIG. 28 is a partial perspective view of the pen injector 50 connected with a pen needle 210 in the dispensing position. For illustrative purposes, in FIGS. 28 and 32, the case 200 is shown as being translucent. As one of ordinary skill in the art will appreciate, the case 200 may be translucent, transparent, or opaque without departing from the scope of the invention. As shown in FIG. 28, an interior side of the case 200 has a guide channel 264 recessed therein. The guide channel 264 guides movement of a boss 216 of the hub 212 within the case 200, and thus guides movement of the pen needle 210 within the case 200. As will be understood by one of ordinary skill in the art, each boss 216 may have a corresponding guide channel 264 in the case 200 without departing from the scope of the present invention. Nevertheless, for clarity and brevity, FIGS. 28-31 illustrate an embodiment with a single guide channel 264.

Figure 29:
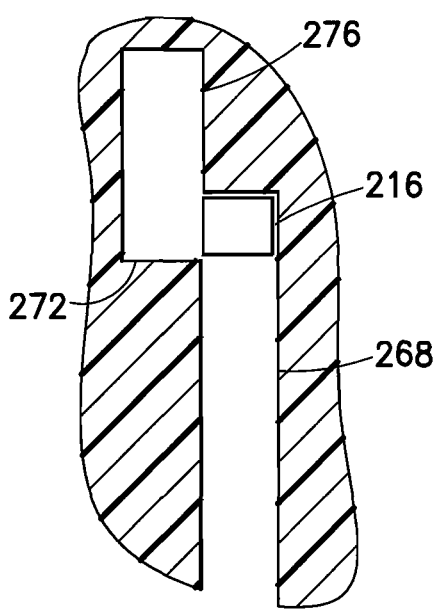
FIGS. 29-31 are partial plan views of a guide channel of the case of FIG. 18.
Figure 30:
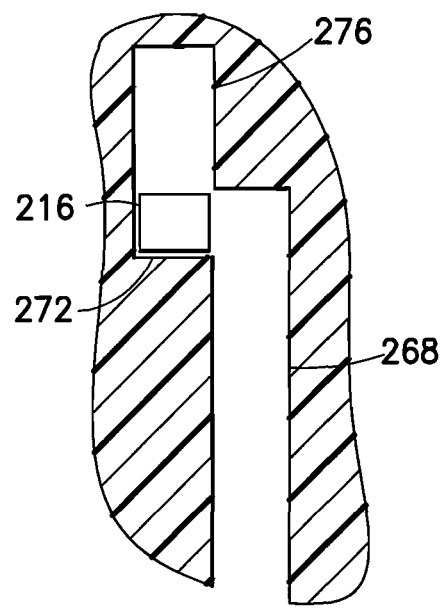
Figure 31:
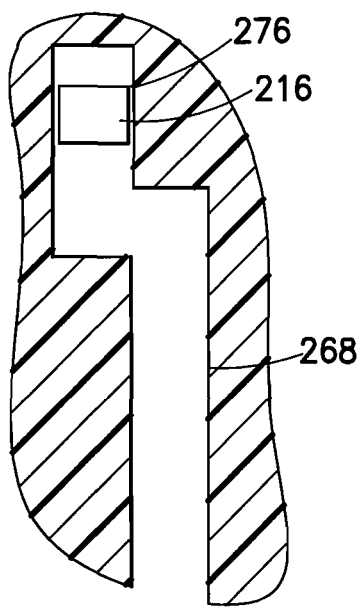

FIGS. 29-31 are partial plan views of the guide channel 264 illustrating movement of the boss 216 during a dispensing operation. FIGS. 28 and 29 illustrate the boss 216 of the pen needle 210 in the dispensing position at a top of a first axial portion 268 of the guide channel 264. Friction between the boss 216 and the top of the first axial portion 268 maintains the boss 216 in the position shown in FIGS. 28 and 29 while the user threads the pen injector 50 into the non-patient end of the hub 212. Once the pen injector 50 and the pen needle 210 are connected tightly, however, additional clockwise (with respect to the top of the case 200) rotation of the pen injector 50 also rotates the hub 212 circumferentially with respect to the case 200. As shown in FIGS. 29 and 30, this circumferential hub rotation slides the boss 216 circumferentially in a lateral portion 272 of the guide channel 264 from the top of the first axial portion 268 to the bottom of a second axial portion 276. From this position, the user can remove the pen needle 210 from the case 200 by pulling the pen injector 50 axially with respect to the case 200, as shown in FIG. 31.

Figure 32:
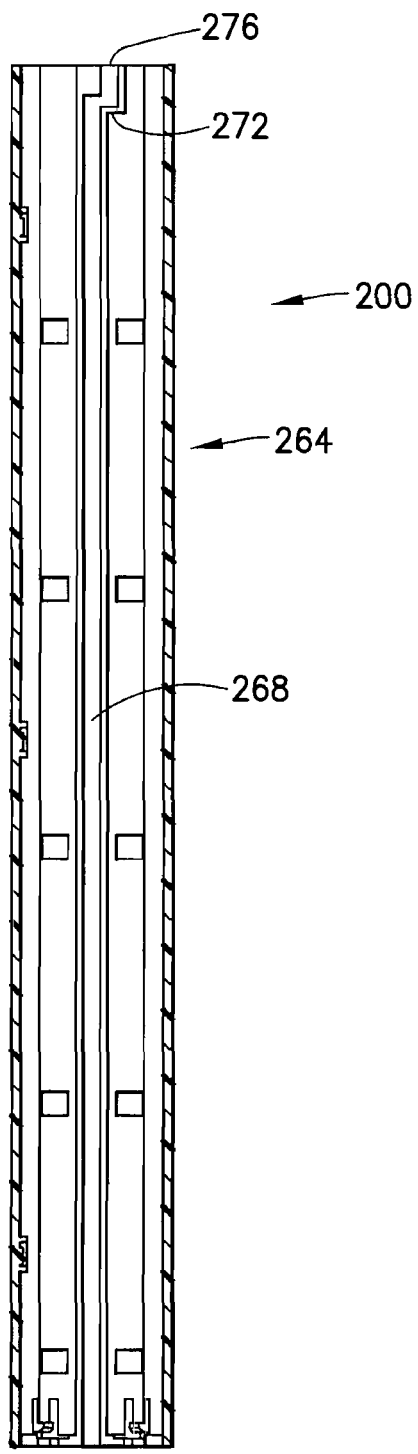
FIG. 32 is a perspective view in cross-section of the case of FIG. 18 with no pen needles disposed therein taken along line 24-24 in FIG. 18.

For instructive purposes, FIG. 32 illustrates an embodiment of the case 200 in which a second guide channel 264 is disposed opposite to the first guide channel 264. FIG. 32 is a perspective view in cross-section taken along line 24-24 in FIG. 18 of the case 200. As shown in FIG. 32, the first axial portion 268 extends from the lateral portion 272 substantially down the remainder of the length of the case 200.

Figure 33:
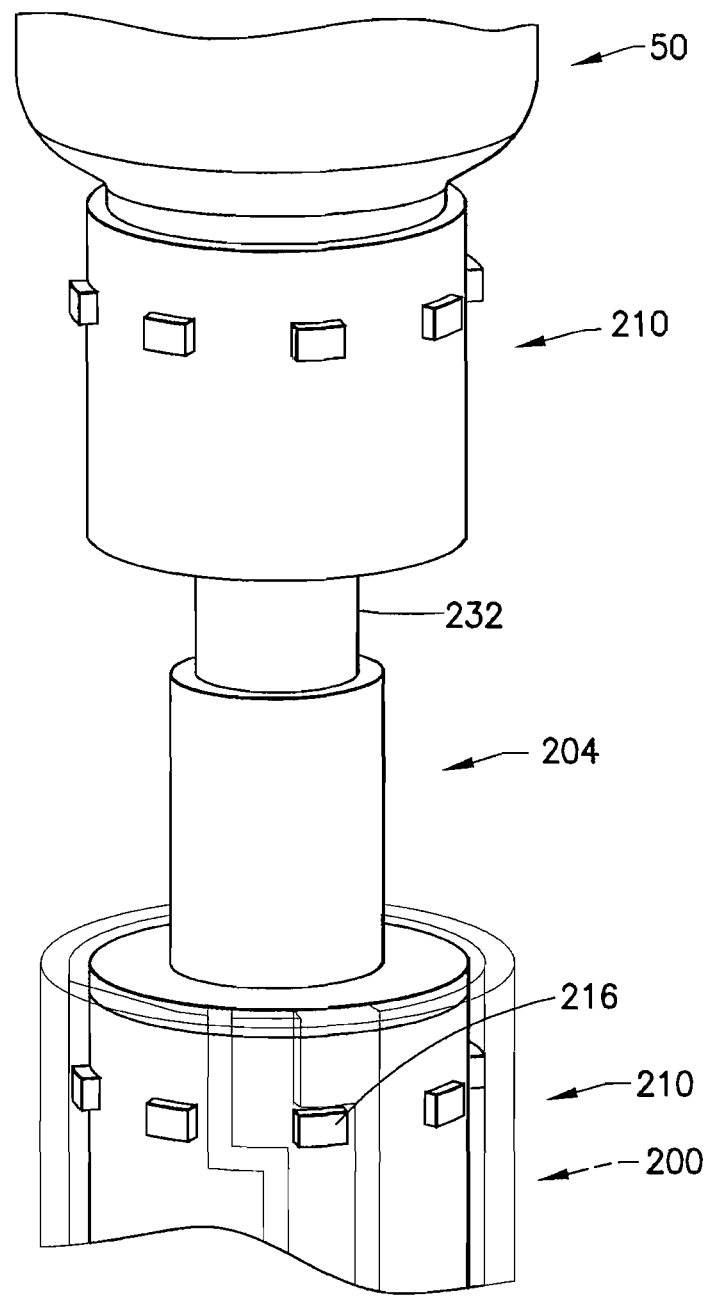
FIG. 33 is a perspective view of the pen injector of FIG. 27, the pen needle of FIG. 19, the needle cover of FIG. 20, the hub cover of FIG. 22, another pen needle of FIG. 19, and the case of FIG. 18.

Because the pen needles 210, needle covers 232, and hub covers 204 are frictionally connected, the axial removal of the top pen needle 210 from the case 200 automatically moves the remaining hub covers 204, pen needles 210, and needle covers 232 axially toward the dispensing end 206 of the case 200. This axial movement is guided by respective bosses 216 disposed in the guide channel 264, and continues until the boss 216 of the next pen needle 210 moves into the dispensing position at the top of the first axial portion 268 as shown in FIG. 33. Further, because the needle cover 232 of the last pen needle 210 is frictionally connected to the separator 208, the axial movement also moves the separator 208.

Figure 34:
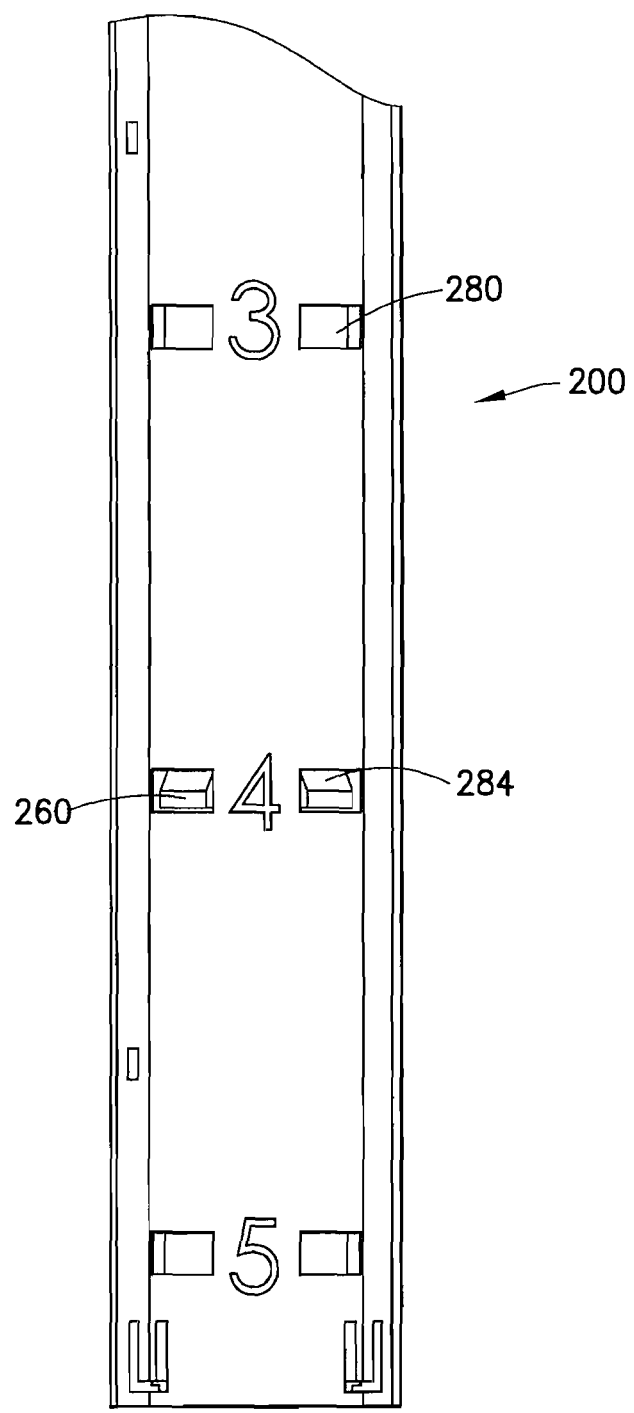
FIG. 34 is a partial perspective view of the case of FIG. 18.

At rest, as shown in FIG. 34, the indicators 260 of the separator 208 extend through holes or detents 280 in the side of the case 200 to indicate the number of remaining pen needles within the case 200. During axial movement of the separator 208 toward the dispensing end 206 of the case 200, sloped faces 284 of the indicators 260 (best seen in FIG. 25) bear against edges of the detents 280, deflecting or elastically deforming the cantilevered legs 256 and drawing indicators 260 within the case 200. When the boss 216 of the next pen needle 210 moves into the dispensing position at the top of the first axial portion 268 (as shown, for example in FIG. 33), the indicators 260 are aligned with the next detents 280 and extend therethrough due to the stored energy of the cantilevered legs 256.

In the illustrated embodiments, there are initially five unused pen needles 210 stored within the case 200. As shown in FIG. 34, after the first pen needle 210 is removed from the case 200, the separator 208 axially moves to a position where the indicators 260 extend through the detents corresponding to the number "4," thereby indicating that four unused pen needles remain within the case 200. Additionally, as will be described in greater detail below, as the separator 208 axially moves to a position where the indicators 260 extend through the next detents 280, space is created between the separator 208 and the storage end 210 of the case 200 for storage of a used pen needle 210.

Figure 35:
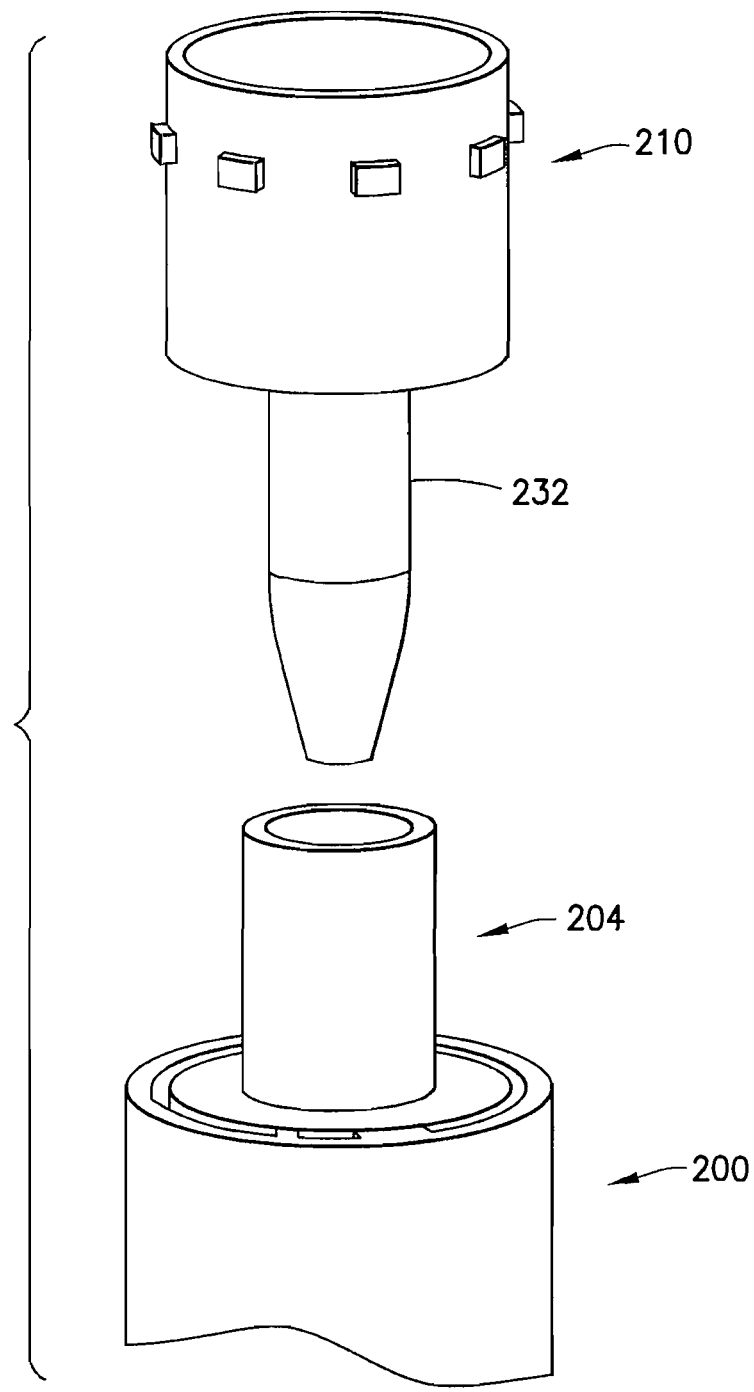
FIG. 35 is a partial perspective view of removal of a pen needle of FIG. 19 and cover of FIG. 20 from a hub cover of FIG. 22.

After the boss 216 of the next pen needle 210 moves into the dispensing position at the top of the first axial portion 268, the user overcomes the frictional resistance between the needle cover 232 of the removed pen needle 210 and the hub cover 204 disposed at the top of the case 200, as shown in FIG. 35. Subsequently, to use the pen needle 210 connected to the pen injector 50, the user removes the needle cover 232 from the protrusion 220. To ensure the above-described axial movement of the hub covers 204, pen needles 210, needle covers 232, and the separator 208 during removal of a pen needle 210 from the case 200, in a hierarchy of tolerances among the pieces, the friction between the needle cover 232 and the protrusion 220 is the greatest. In an alternative embodiment, in which needle covers 232 are omitted, in a hierarchy of tolerances among the pieces, the friction between the protrusion 220 and the next hub cover 204 is the greatest.

Figure 36:
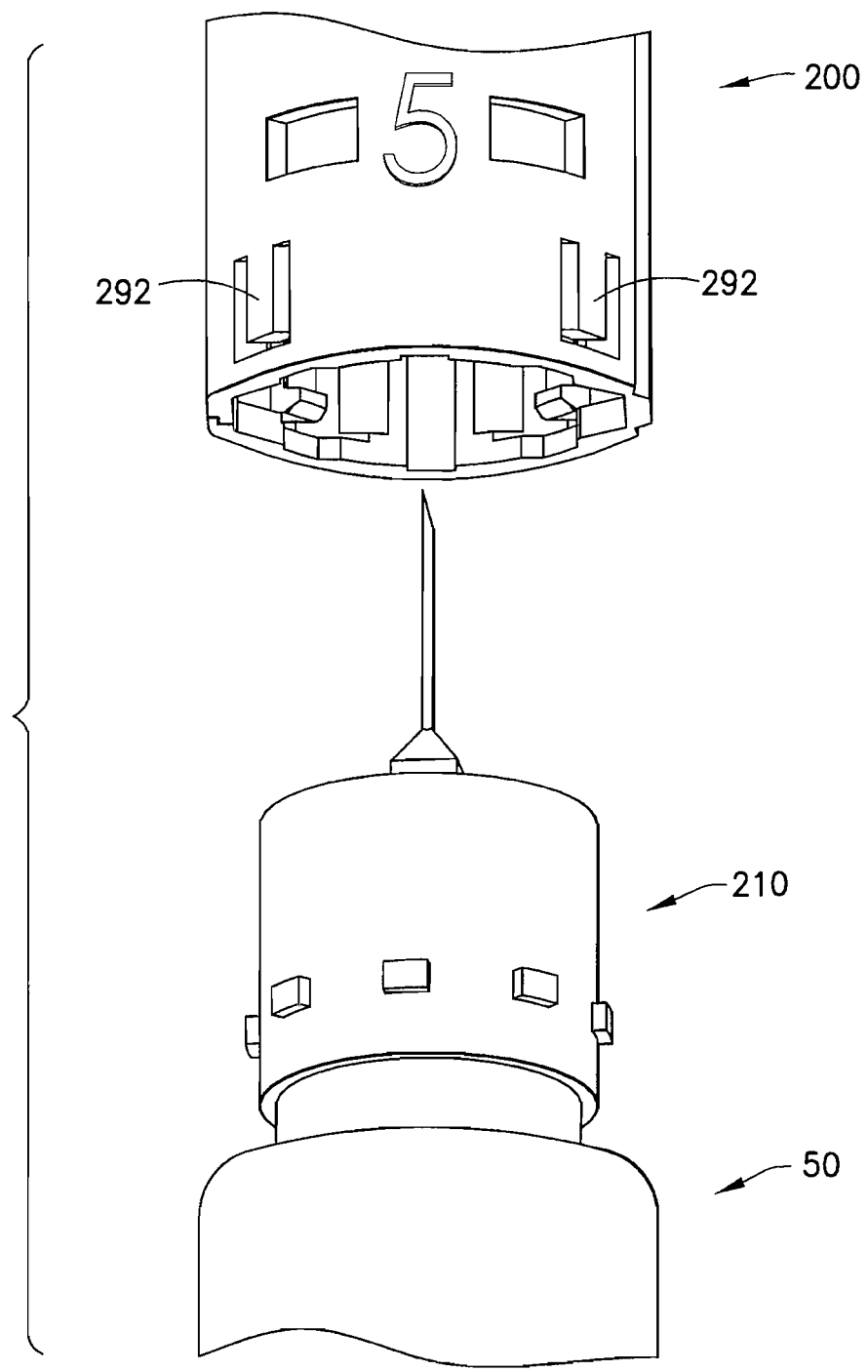
FIGS. 36-38 are partial perspective views of insertion of a pen needle of FIG. 19 into the storage end of the case of FIG. 18.
Figure 37:
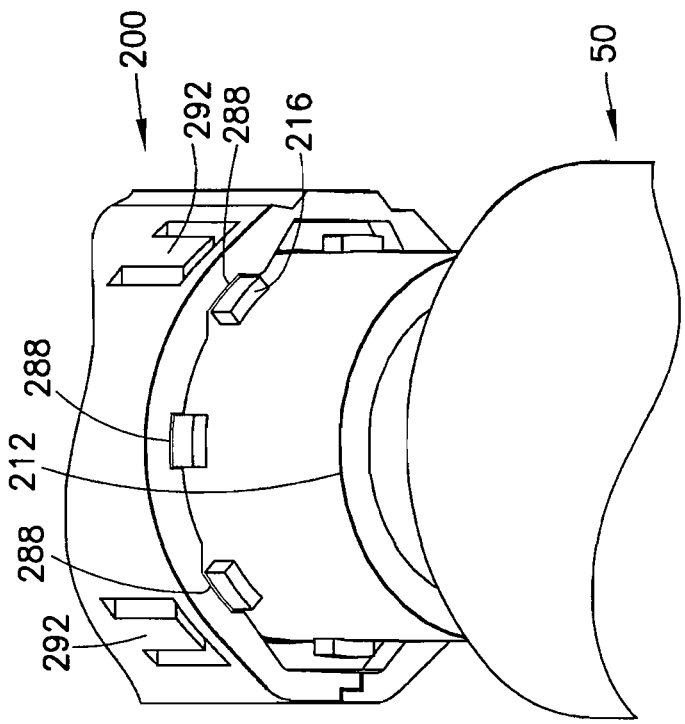

As shown in FIGS. 36 and 37, once the pen needle 210 has been used, the user inserts the used pen needle 210 into the storage end 210 of the case 200, in the space created by the axial movement of the separator 208. Additionally, it is noted that the orientation of the used pen needles 210 within the case 200 is opposite to the orientation of the unused pen needles 210 within the case 200. According to one embodiment, as shown in the enlarged perspective view illustrated in FIG. 37, the storage end 210 of the case 200 includes a plurality of insertion guide channels 288. The insertion guide channels 288 may be angled to ease insertion of the bosses 216 of the used pen needle 210 and ensure circumferential orientation of the used pen needle 210. For example, the insertion guide channels 288 may be angularly-shaped funnels, thus self aligning the used pen needle 210 during insertion thereof into the storage end 210 of the case 200.

Figure 38:
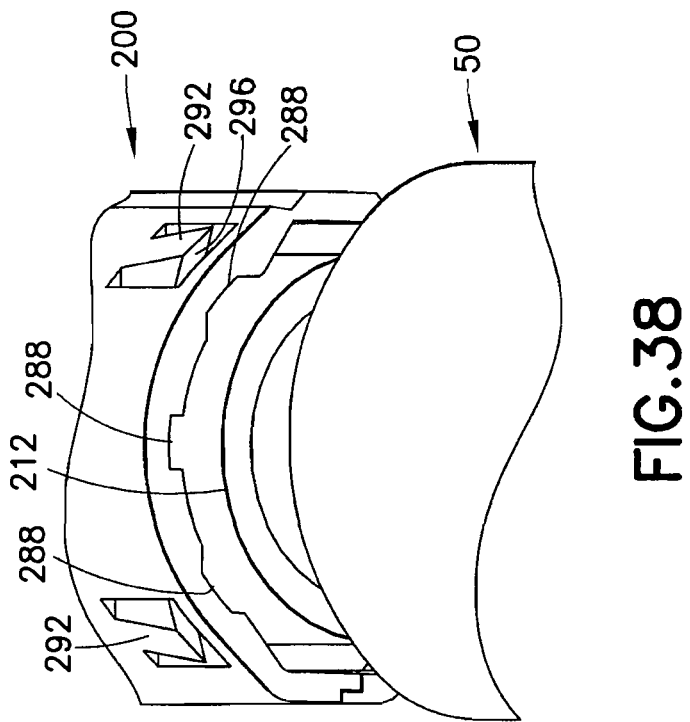

Further, as shown in FIGS. 36-38, a storage end 210 of the case 200 also includes a plurality of cantilevered retention units or pawls 292. As the user further inserts the used pen needle 210 (the motion illustrated between FIGS. 37 and 38), bosses 216 engage respective sloped faces 296 of the pawls 292, and force the cantilevered end of the pawls 292 to extend (deflect or elastically deform) radially with respect to an outer surface of the case 200. The sloped faces 296 have a hook on an interior side thereof, so that as the user even further inserts the used pen needle 210 and the bosses 216 pass the hooks on the sloped faces 296, the pawls 292 return to their initial position. By this action, the hooks engage axial sides of the bosses toward the storage end 210 of the case 200, thereby preventing axial removal of the used pen needle 210 from the storage end 210 of the case 200.

Moreover, anti-rotation features are disposed at both ends of the case 200. At the dispensing end 206 of the case 200, the guide channel 264 prevents rotation of the pen needle 210 to enable attachment of the pen injector 50 to the pen needle 210. Additionally, at the storage end 210 of the case 200, insertion guide channels 288 and pawls 292 prevent rotation of the used pen needle 210 to enable the detachment of the pen injector 50 from the used pen needle 210. Subsequent to unthreading the pen injector 50 from the used pen needle 210, the user axially pulls the pen injector 50 from the storage end 210 of the case 200.

Although not illustrated for brevity, similar to the case 100, the case 200 may have end caps for covering the dispending and storage ends thereof.

Because patients, such as diabetics, are accustomed to using and transporting pen injectors (for example, pen injector 50), another advantage of embodiments of the present invention is to provide a compact, convenient apparatus for dispensing unused pen needles and storing used pen needles in a familiar form factor.

A manual lock can be provided on the pen needle storage assembly, thereby allowing the user to manually lock the storage assembly to allow for safe disposal thereof. Preferably, such a lock becomes functional only after the last pen needle has been used.

In another exemplary embodiment of the present invention, only the last-used pen needle is always accessible, thereby providing an available pen needle in case of emergency. In such an embodiment, the other used pen needles are locked into the storage end of the case and are no longer accessible.

Although only a few embodiments of the present invention have been shown and described, the present invention is not limited to the described embodiments. Instead, it will be appreciated by those skilled in the art that changes may be made to these embodiments without departing from the principles and spirit of the invention, the scope of which is defined by the claims and their equivalents.

What is claimed is:

1. An apparatus for storing and dispensing pen needles for an injection device, the apparatus comprising:
a case having dispensing and storage ends for dispensing and storing a plurality of pen needles and a plurality of needle cover units, each pen needle having a patient end and a hub for connection to the injection device, and each needle cover unit having a needle-covering portion for covering a patient end and a hub-covering portion for covering a hub;
wherein a needle-covering portion covering the needle of one pen needle is coupled with a hub-covering portion covering a hub of another pen needle;
wherein prior to use, a hub-covering portion of a needle cover unit covering the hub of a pen needle is exposed to an outside at the dispensing end of the case, and subsequent to use, a pen needle is stored in the storage end of the case; and
wherein the hub-covering portion of the needle cover unit enters and engages an interior of the needle hub.

2. The apparatus according to claim 1, further comprising a separator displaceably disposed within the case for separating used and unused pen needles and providing a visual indicator of the remaining number of unused pen needles.

3. The apparatus according to claim 2, wherein the separator includes an advancing member disposed on the outside of the case for advancing an unused pen needle toward the dispensing end of the case.

4. The apparatus according to claim 3, wherein the advancing member moves within a track on the case, the track having a plurality of detents for selectively displacing the separator by a predetermined distance.

5. The apparatus according to claim 2, wherein
the needle cover unit is also stored in the storage end of the case, with the needle-covering portion of the needle cover unit covering the patient end of the pen needle; and
wherein the needle cover unit is selectively connectable to the separator.

6. The apparatus according to claim 1, wherein the needle cover unit is also stored in the storage end of the case, with the needle-covering portion of the needle cover unit covering the patient end of the pen needle.

7. The apparatus according to claim 6, wherein unused needle cover units and pen needles are stored in a first orientation relative to the case, and used needle cover units and pen needles are stored in a second orientation opposite to the first orientation.

8. The apparatus according to claim 1, wherein the case includes end caps for selectively closing the dispensing and storage ends.

9. The apparatus according to claim 1, wherein the case includes anti-rotation/retaining structures at the dispensing and storage ends for connecting and disconnecting the injection device with the pen needle.

10. The apparatus according to claim 9, wherein the anti-rotation/retaining structures axially align with the case and protrude radially-inward.

11. The apparatus according to claim 1, wherein the needle cover-covering portion and the hub-covering portion of the needle cover unit are separable from each other.

12. The apparatus according to claim 1, wherein subsequent to the removal of the exposed hub-covering portion of the needle cover unit covering the hub of the pen needle in a dispensing position, removal of the pen needle in the dispensing position from the case automatically displaces remaining unused hub-covering portions, pen needles, and needle-covering portions toward the dispensing end of the case.

13. The apparatus according to claim 12, further comprising
a separator displaceably disposed within the case for separating used and unused pen needles and providing a visual indicator of the remaining number of unused pen needles;
wherein the automatic displacement of the remaining hub-covering portions, pen needles, and needle-covering portions toward the dispensing end displaces a pen needle previously adjacent to the removed pen needle to the dispensing position, displaces the separator toward the dispensing end, and creates a space in the case at the storage end for insertion of the removed pen needle.

14. The apparatus according to claim 13, wherein the separator securely receives the needle-covering portion of the needle cover unit of the last unused pen needle.

15. The apparatus according to claim 13, wherein the case comprises a guide channel on an interior thereof and the hub comprises a boss on an exterior thereof for slidable displacement in the guide channel.

16. The apparatus according to claim 15, wherein the guide channel comprises a first axial portion, a second axial portion disposed at the dispensing end, and a lateral portion connecting the first and second axial portions.

17. The apparatus according to claim 15, wherein the case comprises an anti-rotation/retaining structure at the dispensing end for connecting the injection device with the pen needle; and
wherein the anti-rotation/retaining structure at the dispensing end comprises the guide channel.

18. The apparatus according to claim 11, wherein the hub-covering portion of a pen needle selectively securely receives the needle-covering portion of the needle cover unit of another pen needle.

19. The apparatus according to claim 12, wherein
the case comprises an anti-rotation/retaining structure at the storage end for disconnecting the injection device from the pen needle;
wherein the hub comprises a boss on an exterior thereof; and
wherein the anti-rotation/retaining structure at the storage end comprises insertion guide channels disposed at the storage end for guiding the boss and preventing rotation of the pen needle, and a cantilevered retention unit for retaining the pen needle in the storage end.

20. The apparatus according to claim 19, wherein
the cantilevered retention unit comprises a sloped face displaced by the boss as the boss passes the sloped face during insertion of the pen needle into the storage end; and
wherein the cantilevered retention unit further comprises a hook for retaining the pen needle after the boss passes the hook during insertion of the pen needle into the storage end.

21. A method for dispensing and storing needle cover units and pen needles for an injection device, each pen needle having a patient end and a hub for connection to the injection device, and each needle cover unit having a needle-covering portion for covering a patient end and a hub-covering portion for covering a hub, the pen needles and needle covering units having a first orientation relative to the case at a dispensing end of the case, the method comprising:

at the dispensing end of a case, removing a needle cover unit from a pen needle in a dispensing position;

connecting the injection device to the hub of the pen needle;

at a storage end of the case, inserting the needle cover unit in a second orientation opposite to the first orientation, the hub-covering portion of the needle cover unit entering and engaging an interior of the needle hub; and inserting the pen needle into the storage end of the case in the second orientation, to cover the patient end of the pen needle with the needle covering portion of the needle cover unit.

22. A method for dispensing and storing needle cover units and pen needles for an injection device, each pen needle having a patient end and a hub for connection to the injection device, and each needle cover unit having a needle-covering portion for covering a patient end and a hub-covering portion for covering a hub, the method comprising:

at the dispensing end of a case, removing a hub-covering portion of a needle cover unit from a pen needle in a dispensing position;

connecting the injection device to the hub of the pen needle; and removing the pen needle, wherein removing the pen needle in the dispensing position automatically advances an unused pen needle and a needle cover unit toward the dispensing end of the case.

23. The method according to claim 22, wherein removing the pen needle in the dispensing position also automatically advances a separator toward the dispensing end, the separator dividing an internal volume of the case and indicating the remaining number of unused pen needles.

24. The method according to claim 22, further comprising inserting the pen needle into the storage end of the case in a second orientation opposite to the first orientation.

25. An apparatus for storing and dispensing pen needles for an injection device, the apparatus comprising:

a case having dispensing and storage ends for dispensing and storing a plurality of pen needles and a plurality of needle cover units, each pen needle having a patient end and a hub for connection to the injection device, and each needle cover unit having a needle-covering end for covering a patient end and a hub-covering end for covering a hub;

wherein a needle cover unit covers a hub of a pen needle prior to connection of the pen needle to the injection device, and the needle cover unit covers the patient end of the pen needle during storage in the storage end of the case; and wherein the hub-covering end of the needle cover unit enters and engages an interior of the needle hub during storage.

26. An apparatus for storing and dispensing pen needles for a pen injection device, the apparatus comprising:

a plurality of pen needles, each having a patient end and a hub for connection to the pen injection device;

a plurality of needle covers, for covering the patient end of the pen needle;

a plurality of hub covers, each having a first end for receiving a needle cover and a second end for covering a hub; and a case for storing and dispensing the pluralities of pen needles and needle covers, the case having dispensing and storage ends;

wherein prior to use, a hub cover is exposed to an outside of the case at the dispensing end of the case, the hub cover covering the hub of one of the plurality of pen needles in a dispensing position; and wherein subsequent to the removal of the exposed hub cover, removal of the pen needle in the dispensing position from the case automatically moves the remaining hub covers, pen needles, and needle covers toward the dispensing end of the case and creates a space in the case at the storage end of the case for insertion of the removed pen needle.

* * * * *